United States Patent
Loset et al.

(10) Patent No.: US 10,640,761 B2
(45) Date of Patent: May 5, 2020

(54) MULTIVALENT PHAGE DISPLAY SYSTEMS AND METHODS

(71) Applicant: University of Oslo, Oslo (NO)

(72) Inventors: Geir Age Loset, Oslo (NO); Inger Sandlie, Oslo (NO)

(73) Assignee: University of Oslo, Oslo (NO)

( * ) Notice: Subject to any disclaimer, the term of this patent is extended or adjusted under 35 U.S.C. 154(b) by 298 days.

(21) Appl. No.: 15/406,196

(22) Filed: Jan. 13, 2017

(65) Prior Publication Data
US 2017/0211060 A1    Jul. 27, 2017

Related U.S. Application Data

(62) Division of application No. 13/496,655, filed as application No. PCT/IB2010/002465 on Sep. 21, 2010, now Pat. No. 9,598,692.

(60) Provisional application No. 61/245,710, filed on Sep. 25, 2009.

(51) Int. Cl.
  *C40B 40/10*     (2006.01)
  *C12N 15/10*     (2006.01)
  *C40B 50/06*     (2006.01)

(52) U.S. Cl.
  CPC .......... *C12N 15/1037* (2013.01); *C40B 40/10* (2013.01); *C40B 50/06* (2013.01)

(58) Field of Classification Search
  None
  See application file for complete search history.

(56) References Cited

U.S. PATENT DOCUMENTS

2003/0186322 A1    10/2003    Janda et al.

OTHER PUBLICATIONS

Endemann and Model "Location of filamentous phage minor coat proteins in phage and in infected cells." J Mol Biol. Jul. 21, 1995;250(4):496-506.
Makowski "Structural Constraints on the Display of Foreign Peptides on Filamentous Bacteriophages " (1993), Gene 128: 5-11.
McCafferty et al. "Phage antibodies: filamentous phage displaying antibody variable domains." (1990) Nature 348 (6301): 552-4.
Nilssen "Delta-Phage—a novel helper phage for high-valence pIX phagemid display" (2012) Nucl. Acids Res. 40: e120.
O'Connell et al. "Phage Versus Phagemid Libraries for Generation of Human Monoclonal Antibodies " (2002) J Mol Biol. 321(1):49-56.
Ploss "Membrane insertion and assembly of epitope-tagged gp9 at the tip of the M13 phage" (2011), BMC Microbiol. 11: 211.
Rondot "A helper phage to improve single-chain antibody presentation in phage display." (2001) Nat Biotechnol. 19 (1):75-8.
Smith "Filamentous fusion phage: novel expression vectors that display cloned antigens on the virion surface" (1985) Science 228(4705): 1315-7.
Tian et al. "A Phage Display System with Unnatural Amino Acids" 2004 Journal of the American Chemical Society vol. 126 pp. 15962 to 15963.

(Continued)

*Primary Examiner* — Christian C Boesen
(74) *Attorney, Agent, or Firm* — Casimir Jones, S.C.; J. Mitchell Jones

(57) ABSTRACT

The present invention relates to vectors, methods and systems for polypeptide display and selection. Specifically, the present invention relates to vectors, methods, and systems for multivalent phage display using pIX protein of filamentous phage and helper phage.

11 Claims, 7 Drawing Sheets

Specification includes a Sequence Listing.

(56) References Cited

OTHER PUBLICATIONS

Koivunen et al. "Isolation of a Highly Specific Ligand for the alpha-five-Beta-1 Integrin from a Phage Display Library" 1994 Journal of Cell Biology vol. 124 pp. 373 to 380.
Gao et al. "A method for the generation of combinatorial antibody libraries using pIX phage display" 2002, Proceedings of the National Academy of Sciences USA vol. 99 pp. 12612 to 12616.
XL1-Blue Competent Cells 2004 Stratagene Catalog No. 200249 pp. 1 to 2.
Soltes et al. "On the influence of vector design on antibody phage display" 2007 Journal of Biotechnology vol. 127 pp. 626 to 637.
Blumer et al. "Translational Control of Phage f1 Gene Expression by Differential Activities of the Gen V, VII, IX and VIII Initiation Sites" 1987 Journal of Molecular Biology vol. 197 pp. 439 to 451.
Gao et al. "Making artificial antibodies: A format for phage display of combinatorial heterodimeric arrays" PNAS 96 (11): 6025-30, May 1999.

MULTIVALENT PHAGE DISPLAY SYSTEMS AND METHODS

CROSS-REFERENCE TO RELATED APPLICATION

This application is a divisional of U.S. patent application Ser. No. 13/496,655, filed May 23, 2012 which is a U.S. § 371 U.S. National Phase Entry of pending International Patent Application No. PCT/IB2010/002465, international filing date Sep. 21, 2010, which claims priority to expired U.S. Provisional Patent Application No. 61/245,710, filed Sep. 25, 2009, the contents of which are herein incorporated by reference in their entireties.

FIELD OF THE INVENTION

The present invention relates to vectors, methods and systems for polypeptide display and selection. Specifically, the present invention relates to vectors, methods, and systems for multivalent phage display using pIX protein of filamentous phage and helper phage.

BACKGROUND OF THE INVENTION

Phage display has been intensively used for producing combinatorial antibody libraries and for presentation of combinatorial arrays of peptide elements (see, e.g., Rodi et al, Curr. Opin. Biotechnol., 10:87-93, 1999; Vaughan et al, Nat. Biotechnol., 16:535-539, 1998; Griffiths et al, Curr. Opin. Biotechnol., 9:102-108, 1998; Zwick et al, Curr. Opin. Biotechnol., 9:427-436, 1998; Dall'Acqua et al, Curr. Opin. Struct. Biol., 8:443-450, 1998; Raag et al, Faseb J., 9:73-80, 1995; Barbas et al, Proc. Natl. Acad. Sci. USA, 88:7978-7982, 1991; Kang et al, Proc. Natl. Acad. Sci. USA, 88:4363-4366, 1991; Huse et al, Science, 246:1273-1278, 1989; each herein incorporated by reference in its entirety).

However, many details of the phage particle itself have not been fully elucidated and the possibility of alternative display formats also remains to be explored. The filamentous bacteriophage fd, and similarly M13, consists of a circular, single-stranded DNA molecule surrounded by a cylinder of coat proteins (FIG. 1). The molecular mass of a particle is about $1.6 \times 10^7$ Da, of which 88% is comprised of protein and 12% is comprised of DNA (Berkowitz et al, J. Mol. Biol., 102:531-547, 1976; herein incorporated by reference in its entirety). Approximately 2700 molecules of the major coat protein pVIII surround each phage particle. At one end of the particle, there are five copies each of pIII and pVI that are involved in host-cell binding and in the termination of the assembly process. The other end contains five copies each of pVII and pIX that are hydrophobic peptides of 33 and 32 amino acids, respectively, required for the initiation of assembly and for maintenance of virion stability. While pIII, pVI, and pVIII have been used to display biological molecules, pVII and pIX have historically been less often utilized (Rodi et al, Curr. Opin. Biotechnol., 10:87-93, 1999; Russel et al, J. Virol., 63:3284-3295, 1989; U.S. patent application Ser. No. 10/222,026; each herein incorporated by reference in its entirety).

Initially it had been found that attempts at phage assembly in the absence of pIX almost completely abolish the production of phage. In addition, initial attempts at displaying a fusion protein on pIX suggested that pIX was not functional when fused with another protein at its N-terminus (Endemann et al, J. Mol. Biol., 250:496-506, 1995), suggesting that display would not be feasible using pIX. However, subsequent work has proven the feasibility of using pIX for fusion proteins in phage display (e.g., U.S. patent application Ser. No. 10/222,026 and WO 2010/097411; herein incorporated by reference in their entirety).

However, prior to development of some embodiments of the present invention, application of pIX fusion proteins remained limited to mono- or oligovalent display of protein-of-interest:pIX fusions. Multivalent display is of benefit in certain applications, including but not limited to applications where a reduction in affinity of the retrieved entities is desired (such as when it is desirable to isolate rare and/or weakly binding clones during de novo selection of peptides binding a particular target), or when conducting stability engineering strategies.

Therefore, what is needed is improved methods, systems, and compositions for multivalent phagemid-based phage display.

SUMMARY OF THE INVENTION

The present invention relates to vectors, methods and systems for polypeptide display and selection. Specifically, the present invention relates to vectors, methods, and systems for multivalent phage display using pIX protein of filamentous phage and helper phage.

During the course of developing some embodiments of the present invention, it was determined that multivalent phage display would be possible using vectors, compositions, systems and methods involving use of M13 phage pIX protein and fusions of proteins of interest to M13 phage pIX protein. In some embodiments, a protein of interest-pIX fusion protein is expressed during phage display, leading to display of the fusion protein on viral particles. In some embodiments, such display is achieved using phagemid vectors during phagemid rescue. In some embodiments, phagemid rescue is facilitated by use of helper phage bearing phage vectors that encode M13 phage pIX with wild-type function, where the open reading frame encoding pIX includes at least one suppressor codon. In some embodiments, phagemid rescue is conducted using a suppressor host strain bearing tRNAs that cause suppression of the suppression codons, such that full-length wild-type function pIX protein is expressed by the helper phage during phagemid rescue, resulting in mono- to oligo-valent display of a protein of interest-pIX fusion. In some embodiments, the suppressor codon included in the helper phage vector is an amber suppression codon, and the suppressor host strain is a supE strain (e.g., XL1-Blue (supE44)). In some embodiments, use of a second nonsuppressor host strain that does not bear a suppressor tRNA results in expression of truncated pIX protein from the helper phage vector (i.e., where the suppressor codons are read as "stop" rather than as coding for an amino acid). In some embodiments, the nonsuppressor host is *E. coli* TOP10F'. In some embodiments, phagemid rescue under conditions where a nonsuppressor host strain is used results in multivalent display of a protein of interest-pIX fusion (FIG. 2).

Methods, systems, compositions and vectors of the present invention are not limited by the type of suppressor codon used in an open reading frame encoding M13 phage pIX. Suppressor codons include amber (5'-TAG-3'), opal (5'-TGA-3'), and ochre (5'-TAA-3'). Methods, systems, compositions and vectors of the present invention are not limited by the number of suppressor codons included in an M13 open reading frame encoding pIX. In some embodiments, more than one suppressor codon is included. Methods, systems, compositions and vectors of the present invention are not limited by the position of suppressor codon(s) included in an M13 open reading frame encoding pIX. In some embodiments, a suppressor codon is present at a position corresponding to or following amino acid 3 of pIX protein. In some embodiments, codons for additional (e.g., non-native) amino acids are included (e.g., inserted) into the pIX open reading frame bearing at least one suppressor codon(s). In some embodiments, no codons for additional (e.g., non-native) amino acids are included (e.g., inserted) into the pIX open reading frame bearing at least one suppressor codon(s). In some embodiments, modifications at or near the amino-terminus of the pIX open reading frame are preferred (e.g., to modifications made at or near the carboxy-terminus).

In some embodiments, wild-type pVII function is preserved in the helper phage strain. In some embodiments, wild-type pVIII function is preserved in the helper phage strain. In some embodiments, no modifications are made to the pIX open reading frame within positions corresponding to the first amino acids of the encoded pIX protein. In some embodiments, no modifications are made to the pIX open reading frame within positions corresponding to the last six to eight, preferably eight amino acids of the encoded pIX protein.

In some embodiments, the pIX open reading frame is permanently destroyed. Such permanent destruction of the pIX open reading frame may be achieved, e.g., by inserting at least one non-suppressible stop codons in a region not interfering with pVII or pVIII translation (e.g., not within the first two codons or last six codons of pIX), or by deleting, modifying, mutating, or otherwise altering the pIX open reading frame. In some embodiments, complementation of pIX is achieved using an exogenous source of pIX. In some embodiments, an exogenous source of pIX is a dedicated host cell packaging line bearing a copy of an open reading frame for M13 phage pIX in its genome, such that expression of this open reading frame results in production of pIX with wild-type function. In some embodiments, an exogenous source of pIX is provided by co-propagation of a helper plasmid containing an open reading frame encoding M13 phage pIX with wild-type function.

Accordingly, in some embodiments, the present invention provides a nucleic acid comprising an open reading frame encoding M13 phage gene pIX, wherein the open reading frame comprises at least one non-wildtype suppressible stop codon. In some embodiments, the non-wildtype suppressible stop codon is selected from the group consisting of amber, ochre, and opal stop codons. In some embodiments, the non-wildtype suppressible stop codon occurs at or following a position corresponding to amino acid three of the open reading frame encoding gene pIX. In some embodiments, the nucleic acid encodes an amino acid sequence at least 50% identical to SEQ ID NO:3, with the proviso that the open reading frame includes at least one non-wildtype suppressible stop codon. In some embodiments, the present invention provides a vector comprising a nucleic acid comprising an open reading frame encoding M13 phage gene pIX, wherein the open reading frame comprises at least one non-wildtype suppressible stop codon. In some embodiments, the present invention provides a phage comprising a nucleic acid comprising an open reading frame encoding M13 phage gene pIX, wherein the open reading frame comprises at least one non-wildtype suppressible stop codon. In some embodiments, the present invention provides a nucleic acid comprising an open reading frame encoding phage gene pIX, wherein said open reading frame comprises at least one non-wildtype suppressible stop codon and is at least 80%, 90%, 95%, 97% or 99% identical to SEQ ID NO:2. In some embodiments, the present invention provides a nucleic acid comprising an open reading frame encoding phage gene pIX, wherein said open reading frame comprises at least one non-wildtype suppressible stop codon and encodes a polypeptide at least 80%, 90%, 95%, 97% or 99% identical to SEQ ID NO: 1. In some embodiments, the open reading frame encoding phage gene pIX comprises two non-wildtype suppressible stop codons. In some embodiments the one or more stop codons are either amber, ochre or opal stop codons. In some embodiments, the present invention provides a nucleic acid comprising an open reading frame encoding phage gene pIX, wherein said open reading frame comprises at least one non-wildtype suppressible stop codon and is at least 80%, 90%, 95%, 97% or 99% identical to SEQ ID NO:4. In some embodiments, the present invention provides a nucleic acid comprising an open reading frame encoding phage gene pIX, wherein said open reading frame comprises at least one non-wildtype suppressible stop codon and encodes a polypeptide at least 80%, 90%, 95%, 97% or 99% identical to SEQ ID NO:3.

In some embodiments, the present invention provides methods for multivalent phage display comprising: a) providing a non-suppressor host strain comprising a phagemid encoding an open reading frame comprising a pIX nucleic acid sequence operably linked to a nucleic acid sequence encoding a protein of interest, wherein expression of the open reading frame results in production of a protein of interest-pIX fusion protein; b) providing a helper phage comprising a nucleotide sequence encoding an open reading frame comprising a pIX nucleic acid sequence, wherein the pIX nucleic acid sequence comprises at least one non-wildtype suppressible stop codon; and c) infecting the non-suppressor host strain with the helper phage under conditions such that the non-suppressor host cell produces phages that display multiple copies of the protein of interest-pIX fusion protein. In some embodiments, the non-wildtype suppressible stop codon is selected from the group consisting of amber, ochre, and opal stop codons. In some embodiments, the at least one non-wildtype suppressible stop codon occurs at or following a position corresponding to amino acid three of the open reading frame encoding gene pIX. In some embodiments, the non-wildtype suppressible stop codon is an amber codon. In some embodiments, the non-suppressor host strain is *E. coli*. In some embodiments, the non-suppressor host strain is *E. coli* TOP10F'.

In some embodiments, the present invention provides systems for phage display comprising: a) a phagemid capable of modification by inclusion of a nucleotide sequence encoding a protein of interest, the nucleotide sequence operably linked to an open reading frame encoding M13 phage pIX; and b) a phage comprising a nucleic acid comprising an open reading frame encoding M13 phage gene pIX, wherein the open reading frame comprises at least one non-wildtype suppressible stop codon. In some embodiments, the systems further comprise a suppressor host strain. In some embodiments, the suppressor host strain is selected from the group consisting of strains having a supE, SupC or SupF genotype. In some embodiments, the systems further comprise a non-suppressor host strain. In some embodiments, the non-suppressor host strain is selected from, but not limited to, the group (and their derivatives) of MC1061, HB2151, ER2738, JM101, DH5αF and TOP10F'. In some embodiments, the non-suppressor host strain is TOP10F'.

Additional embodiments will be apparent to persons skilled in the relevant art based on the teachings contained herein.

DEFINITIONS

Figure 1:
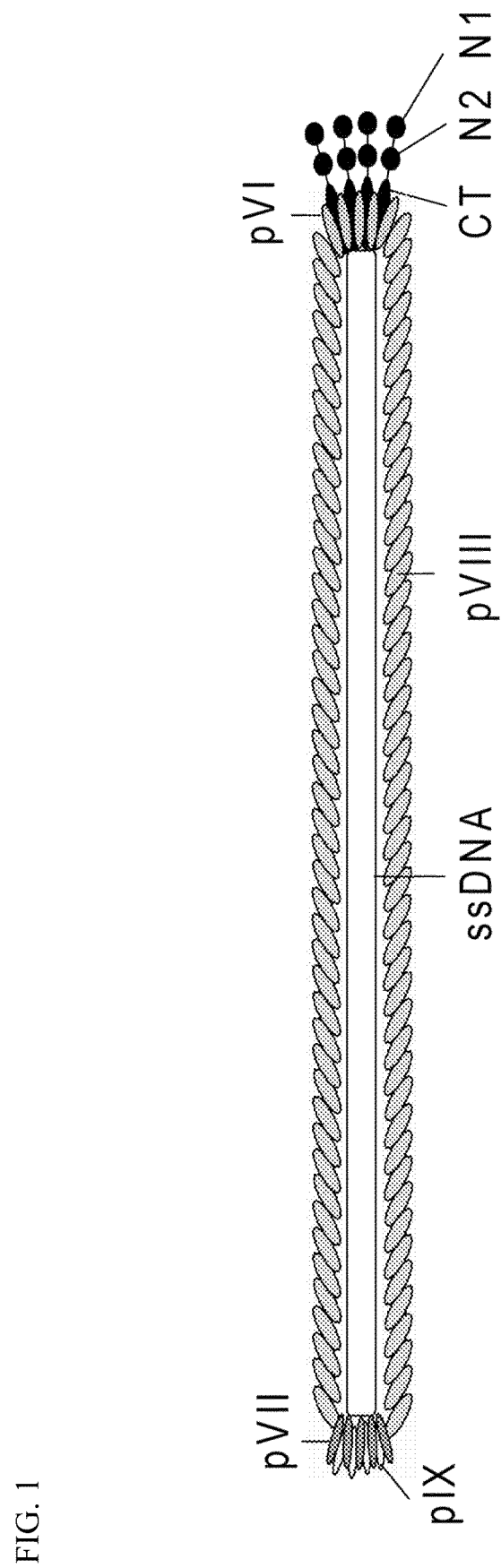
FIG. 1 Schematic drawing of the filamentous phage structure. The virion is built up by five structural proteins that coat a single-stranded DNA molecule. In the wild type (wt) phage there are about 2700 copies of pVIII and approximately 3-5 copies of either of the four proteins pIII, pVI, pVII and pIX, which are found at each tip of the virion. Virion size is dependent on the genome size at approx. 2.3 nucleotides per pVIII coat protein and thus the length of the particle is accommodated by an increase or decrease in the inserted copies of pVIII. Notably, the pIII and pVIII structures have been characterized by x-ray fiber diffraction, crystallography and NMR. The minor coat protein pIII contains three distinct domains separated by glycin-rich regions: N1 (binds to TolA), N2 (binds to the F pilus) and CT (integrated into the virion and is important for normal virion assembly).

To facilitate an understanding of the present invention, a number of terms and phrases are defined below:

As used herein, the term "phage", often called bacteriophage, is here meant as a virus infecting, replicating and which is secreted from bacteria. A filamentous bacteriophage, or filamentous phage, is a phage with a single stranded DNA molecule (ssDNA) which is packaged with phage coat proteins. The secreted filamentous phage particle has phenotypically a filamentous structure.

As used herein, the term "filamentous phage" encompasses both phage genome-derived virions and phagemid-derived virions.

As used herein, the term "helper phage" refers to a virus which helps a separate and unrelated defective viral vector (e.g., a phagemid) to reproduce by infecting a host cell containing the viral vector and providing the proteins which the viral vector requires to form virions containing the viral vector.

As used herein, the term "phagemid" or "phasmid" is a type of cloning vector developed as a hybrid of the filamentous phage and plasmids to produce a vector that can propagate as a plasmid, and also be packaged as single stranded DNA in viral particles. Similarly to a plasmid, a phagemid can be used to clone DNA fragments and be introduced into a bacterial host by a range of techniques (transformation, electroporation). However, infection of a bacterial host containing a phagemid with a 'helper' phage, for example VCSM13 or M13K07, provides the necessary viral components to enable single stranded DNA replication and packaging of the phagemid DNA into phage particles.

As used herein, the term "display" refers to the presence (e.g., expression) of a protein on the surface of a phage particle. The term "phage particle" is used interchangeably with the term "virion". In some embodiments, the protein is a protein of interest. In some embodiments, the protein of interest is fused to a phage protein. In some embodiments, the phage protein is pIX.

As used herein, the term "fusion" or "fusion protein" refers to the covalent association of a protein of interest (e.g., a non-phage protein, an exogenous protein) with a phage protein. In some embodiments, the phage protein is pIX. Fusion may occur preferably at or near the N-terminus of the phage protein, but may occur at other sites, e.g., internal or C-terminal sites.

As used herein, the term "multivalent" or "polyvalent" refers to the presence of more than one protein of a single type (e.g., a protein of interest:phage protein fusion) on the surface of a phage particle.

As used herein, the term "monovalent" refers to the presence of one protein of a single type (e.g., a protein of interest:phage protein fusion) on the surface of a phage particle.

As used herein, the term "protein of interest" refers to any protein which one of skill in the art wishes to study. Typically, a protein of interest is not encoded by a phage genome. Proteins of interest are not limited by biochemical, enzymatic, structural, or physiological function or lack thereof. Neither are proteins of interest limited by size, origin (e.g., species from which they are derived), or whether present in nature or synthesized. Proteins of interest may be "wild-type" or "mutant", intact or fragmented relative to a reference protein. Proteins of interest that have been studied using phage display include but are not limited to enzymes (including but not limited to kinases, phosphatases, proteases, polymerases, adenylate cyclases, ligases, etc.), molecular chaperones, receptors, structural proteins, antigens, synthetic (e.g, non-natural) proteins, antibodies and antibody fragments (e.g., Fab fragments), T cell receptors and fragments thereof, major histocompatibility complex molecules and fragments thereof, DNA-binding proteins, drug targets (e.g., proteins of interest that are screened for ligand interaction, e.g. with ligand types including but not limited to enzyme inhibitors, receptor agonists and antagonists), and hormones. Proteins of interest may include subjects of directed evolution studies.

As used herein, the term "suppressible stop codon" refers to a stop codon that is read in certain host cell strains containing a genotype that allows a tRNA to recognize the suppressible stop codon.

As used herein, the term "suppressor host strain" refers to a host cell strain that contain a suppressor genotype that allows the reading of a particular suppressible stop codon.

As used herein, the term "non-suppressor strain" refers to a host cell strain that does not have a suppressor genotype that allows the reading of a particular suppressible stop codon.

As used herein, the term "non-wildtype suppressible stop codon" refers to suppressible stop codon that is present in a nucleotide sequence that does not naturally contain such a suppressible stop codon, i.e., the wildtype version of the nucleic acid sequence does not contain a suppressible stop codon.

The term "gene" refers to a nucleic acid (e.g., DNA or RNA) sequence that comprises coding sequences necessary for the production of an RNA, and/or a polypeptide, or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" may also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' untranslated sequences. The sequences which are located 3' or downstream of the coding region and which are present on the mRNA are referred to as 3' non-translated sequences. The term "gene" encompasses both cDNA and genomic forms of a gene. In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

The term "heterologous gene" refers to a gene encoding a factor that is not in its natural environment (i.e., has been altered by the hand of humans). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise cDNA forms of the gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The terms "region" or "portion" when used in reference to a nucleic acid molecule refer to a set of linked nucleotides that is less than the entire length of the molecule.

The term "strand" when used in reference to a nucleic acid molecule refers to a set of linked nucleotides which comprises either the entire length or less than or the entire length of the molecule.

The term "linker" when used in reference to a nucleic acid molecule refers to a nucleotide region which joins two other regions or portions of the nucleic acid molecule; such connecting means are typically though not necessarily a region of a nucleotide.

The term "a polynucleotide having a nucleotide sequence encoding a gene" or "a polynucleotide having a nucleotide sequence encoding a gene" or "a nucleic acid sequence encoding" a specified RNA molecule or polypeptide refers to a nucleic acid sequence comprising the coding region of a gene or in other words the nucleic acid sequence which encodes a gene product. The coding region may be present in cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. This is also of importance in efficacy of RNAi inhibition of gene expression or of RNA function.

As used herein, similarity between two polypeptides or nucleic acids refers to the relatedness between the sequence of amino acids of the polypeptides or the nucleotide sequences of the nucleic acids. Similarity can be based on the degree of identity and/or homology of sequences of residues and the residues contained therein.

Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. Identity refers to the extent to which the amino acid or nucleotide sequences are invariant. Alignment of amino acid sequences, and to some extent nucleotide sequences, also can take into account conservative differences and/or frequent substitutions in amino acids (or nucleotides).

Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

Identity per se has an art-recognized meaning and can be calculated using published techniques. While there exists a number of methods to measure identity between two polynucleotide or polypeptides the term identity is well known to skilled artisans (Carillo, H. & Lipton, D., SIAM J Applied Math 48:1073 (1988)). For sequence comparison, typically one sequence acts as a reference sequence to which test sequences are compared. When using a sequence comparison algorithm, test and reference sequences are input into a computer, subsequent coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol 215:403-410 (1990)). These initial neighborhood word hits act as seeds for initialing searches to find longer HSPs containing them. The word hits are then extended in both directions along each sequence for as far as the cumulative alignment score can be increased. Cumulative scores are calculated using, for nucleotide sequences, the parameters IvI (reward score for a pair of matching residues; always >0) and N (penalty score for mismatching residues; always <0).

For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

As used herein, the terms "percent identity" and "percent identical" (with respect to nucleic acid and/or amino acid sequences) are used interchangeably with "percent homology" unless otherwise indicated. In general, for determination of the percentage homology or identity, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Parti, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48: 1073). By sequence homology, the number of conserved amino acids is determined by standard alignment algorithms programs, and can be used with default gap penalties established by each supplier.

Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two molecules have nucleotide sequences or amino acid sequences that are identical or homologous can be determined using known computer algorithms such as the FASTA program, using for example, the default parameters as in Pearson et al. (1988) Proc. Natl. Acad. Sci. USA 55:2444 (other programs include the GCG program package (Devereux, J., et al., Nucleic Acids Research 12(I):3%1 (1984)), BLASTP, BLASTN, FASTA (Altschul, S. F., et al., J Mol. Biol. 215:403 (1990)); Guide to Huge Computers, Martin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar MegAlign program (Madison, Wis.) and the University of Wisconsin Genetics Computer Group (UWG) Gap program (Madison Wis.).

Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman (1981) Adv. Appl. Math. 2:482). Briefly, the GAP program defines similarity as the number of aligned symbols (i.e., nucleotides or amino acids), which are similar, divided by the total number of symbols in the shorter of the two sequences.

Default parameters for the GAP program can include: (1) a unary comparison matrix (containing a value of 1 for identities and 0 for non-identities) and the weighted comparison matrix of Gribskov et al. (1986) Nucl. Acids Res. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term identity or homology represents a comparison between a test and a reference polypeptide or polynucleotide. As used herein, the term at least 90% identical to refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g., 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$•H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$•H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$•H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "vector" refers to nucleic acid molecules that transfer DNA segment(s) from one cell to another, and includes those nucleic acid molecules that are viral in origin. The term "vehicle" is sometimes used interchangeably with "vector." A vector may be used to transfer an expression cassette into a cell; in addition or alternatively, a vector may comprise additional genes, including but not limited to genes which encode marker proteins, by which cell transfection can be determined, selection proteins, be means of which transfected cells may be selected from non-transfected cells, or reporter proteins, by means of which an effect on expression or activity or function of the reporter protein can be monitored. The term "vector" includes phage and phagemid vectors.

The term "expression cassette" refers to a chemically synthesized or recombinant DNA molecule containing a desired coding sequence and appropriate nucleic acid sequences necessary for the expression of the operably linked coding sequence either in vitro or in vivo. Expression in vitro includes expression in transcription systems and in transcription/translation systems. Expression in vivo includes expression in a particular host cell and/or organism.

Nucleic acid sequences necessary for expression in prokaryotic cell or in vitro expression system usually include a promoter, an operator (optional), and a ribosome binding site, often along with other sequences. Eukaryotic in vitro transcription systems and cells are known to utilize promoters, enhancers, and termination and polyadenylation signals. Nucleic acid sequences useful for expression via bacterial RNA polymerases, referred to as a transcription template in the art, include a template DNA strand which has a polymerase promoter region followed by the complement of the RNA sequence desired. In order to create a transcription template, a complementary strand is annealed to the promoter portion of the template strand. However, the present invention is not limited to any particular configuration and all known systems are contemplated.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

DETAILED DESCRIPTION OF THE INVENTION

Figure 2C:
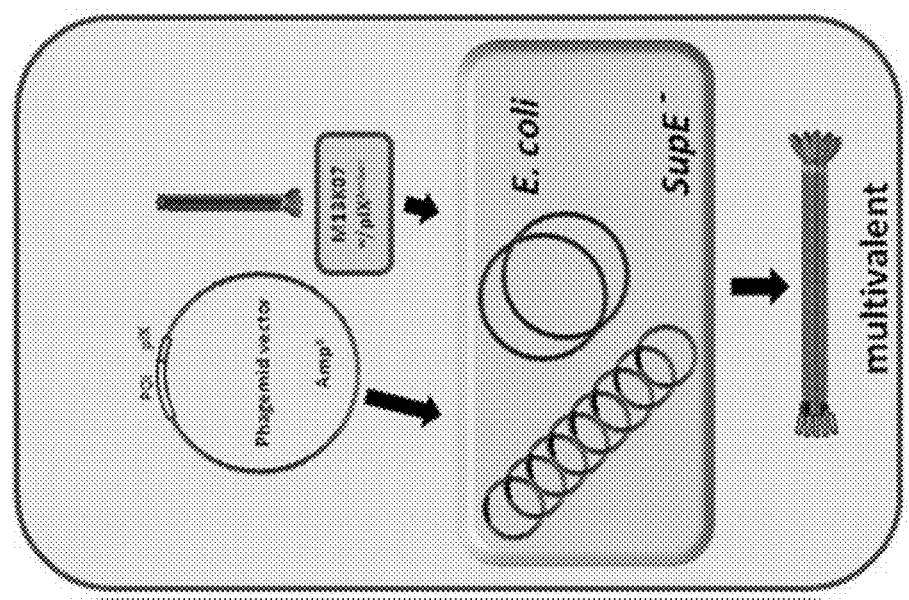
FIG. 2A-C Illustration schematically showing the phagemid rescue routs using a standard phagemid system (A) and the M13K07 pIX$^{Amber}$ mutant with either a supE positive (B), or negative (C) host. The phagemid is selectively propagated in the *E. coli* host based on the ampicillin resistance marker. For virion assembly to occur, the host is super-infected with a helper phage containing all elements necessary for new virion assembly. The helper phage has a defect in the replicative system whereas the phagemid is a high copy number plasmid; hence the amount of DNA from these two sources differs in favor of the phagemid. This normally ensures that the phagemid is preferentially encapsulated into the virion body giving rise to the physical coupling between the phenotype (the POI) and the genotype (the phagemid). In A, monovalent POI-pIX display is achieved, whereas in B mono- to oligovalent display is achieved. In C, there is no pIX complementation from the helper phage; hence multivalent display is achieved, meaning that all five pIX copies on the virion display the POI.
Figure 2B:
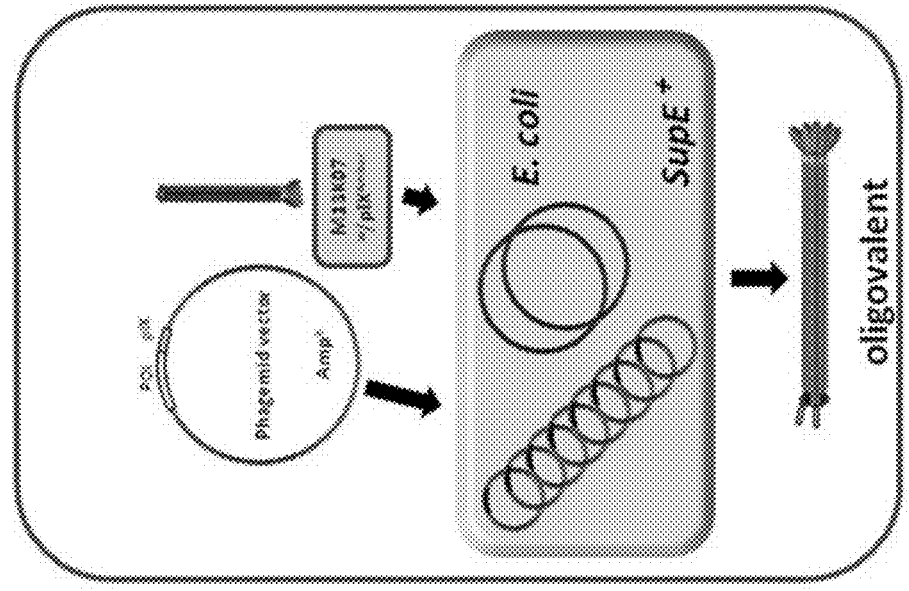
Figure 2A:
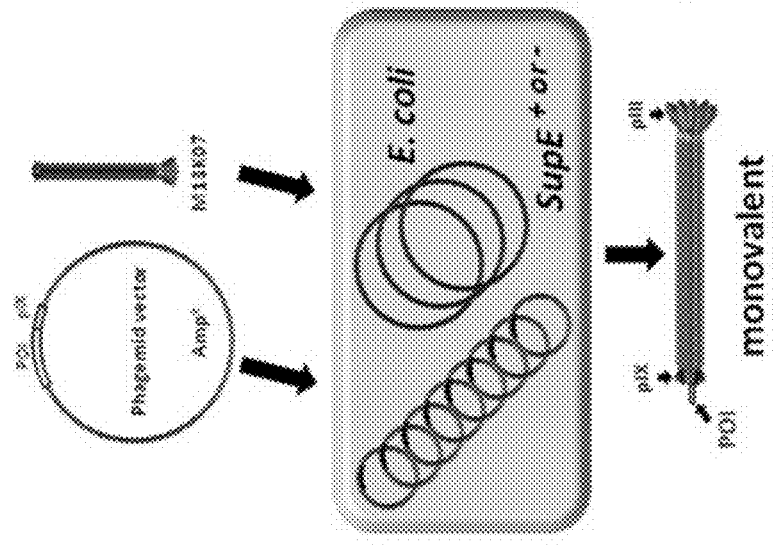

In phagemid-based phage display, phagemid propagation directs synthesis of a protein of interest (POI)-capsid fusion in the proper *E. coli* host and thereafter packaging the POI-capsid fusion into functional virions by superinfecting the host with a genetically modified wild-type phage virion that supports new virion assembly (FIG. 2A). This process is termed phagemid rescue (Bradbury et al. (2004) J. Immunol. Meth. 290:29-49; herein incorporated by reference in its entirety). Such modified wild-type phages are called helper phages. When such a method is used, there are therefore two sources of capsid protein upon rescue: capsid protein arising from the phagemid itself, and capsid protein arising from the helper phage genome. The rescued virions will thus contain a mixture of phagemid-derived fusion (POI) capsid protein and wild-type capsid protein, resulting in mono- to oligovalent POI display. This may be a desired form of display for some applications (e.g., high affinity selection versions of the POI towards a defined ligand) (Hoogenboom (2005) Nature Biotech. 23:1105-1116; herein incorporated by reference in its entirety).

In certain embodiments of the present invention, destruction of the open reading frame (ORF) of the wild-type capsid protein in the helper phage genome (i.e., the very same capsid protein that is also found on the phagemid) results in the phagemid serving as the only genetically functional source of the capsid protein. Therefore, this results in multivalent POI display (Rondot et al. (2001) Nature Biotech. 19:75-78; Baek et al. (2002) Nucleic Acids Res. E18; Soltes et al. (2003) J. Immunol. Meth. 274:233-244; each herein incorporated by reference in its entirety). Multivalent display has proven superior in facilitating discovery of new POI specificities towards defined ligands (O'Connell et al. (321) J. Mol. Biol. 321:49-56; herein incorporated by reference in its entirety), generally with a reduction in affinity of the retrieved entities as compared to low valence display. Moreover, multivalent display effectively supports many stability engineering strategies using phage display (Jespers et al. (2004) Nature Biotech. 22:1161-1165; herein incorporated by reference in its entirety).

In some embodiments of the present invention, the pIX ORF within a helper phage genome is modified to encode suppressible stop codons (e.g., amber, opal, or ochre stop codons; see, e.g., Examples 1-2). Amber mutations were the first set of nonsense mutations to be discovered (Stahl (1995) Genetics 141:439-442). Viruses with amber mutations are characterized by their ability to only infect certain strains of bacteria, known as amber suppressors. These bacteria carry their own tRNA mutation which allows a recovery of function in the mutant viruses, e.g., a mutation in the tRNA which recognizes the amber stop codon allows translation to "read through" the codon and produce full length protein, thereby recovering the normal form of the protein and "suppressing" the amber mutation. Thus, amber mutants are an entire class of virus mutants which can grow in bacteria that contain amber suppressor mutations. In some embodiments, the present invention provides a nucleic acid comprising an open reading frame encoding phage gene pIX, wherein said open reading frame comprises at least one non-wildtype suppressible stop codon and is at least 80%, 90%, 95%, 97% or 99% identical to SEQ ID NO:2. In some embodiments, the present invention provides a nucleic acid comprising an open reading frame encoding phage gene pIX, wherein said open reading frame comprises at least one non-wildtype suppressible stop codon and encodes a polypeptide at least 80%, 90%, 95%, 97% or 99% identical to SEQ ID NO: 1. In some embodiments, the open reading frame encoding phage gene pIX comprises two non-wildtype suppressible stop codons. In some embodiments the one or more stop codons are either amber, ochre or opal stop codons. In some embodiments, the present invention provides a nucleic acid comprising an open reading frame encoding phage gene pIX, wherein said open reading frame comprises at least one non-wildtype suppressible stop codon and is at least 80%, 90%, 95%, 97% or 99% identical to SEQ ID NO:4. In some embodiments, the present invention provides a nucleic acid comprising an open reading frame encoding phage gene pIX, wherein said open reading frame comprises at least one non-wildtype suppressible stop codon and encodes a polypeptide at least 80%, 90%, 95%, 97% or 99% identical to SEQ ID NO:3.

The ochre mutation was the second stop codon mutation to be discovered. Given a color name to match the name of amber mutants, ochre mutant viruses had a similar property in that they recovered infectious ability within certain suppressor strains of bacteria. The set of ochre suppressors was distinct from amber suppressors, so ochre mutants were inferred to correspond to a different nucleotide triplet. Through a series of mutation experiments comparing these mutants with each other and other known amino acid codons, it was found that the amber and ochre mutations corresponded to the nucleotide triplets "UAG" and "UAA" (Brenner et al. (1965) Nature 206:994-998).

The third and last stop codon in the standard genetic code was discovered soon after, corresponding to the nucleotide triplet "UGA" (Brenner et al. (1967) Nature 213:449-450). Nonsense mutations that created this premature stop codon were later called opal mutations or umber mutations.

Modification of the pIX ORF to include a suppressible stop codon may for example lead to a functional ORF in a suppressor host strain, whereas protein translation is compromised in a non-suppressor strain. Consequently, in some embodiments of the present invention, the helper phage genome can be propagated normally in an appropriate suppressor host strain, which also can produce normal helper phage virions, whereas conducting pIX-based phagemid rescue in combination with a non-suppressor strain results in production of multivalent POI as a pIX phagemid fusion protein.

A. Phage Display Systems

In some embodiments, the present invention provides vectors, systems and methods for producing a filamentous phage comprising a matrix of proteins encapsulating a genome or a phagemid encoding a fusion protein (protein). The fusion protein comprises an exogenous polypeptide portion fused near the amino terminus of a filamentous phage pIX protein as described herein.

The term "phage display" generally refers to a set of techniques for the display and selection of polypeptides on the surface of particles produced from a replicable genetic package (e.g., a bacteriophage). As first described by Smith in 1985 for the display of EcoRI endonuclease (Smith et al. (1985) *Science* 228: 1315-17), phage display methods comprise expressing a polypeptide of interest as a fusion protein attached to a bacteriophage coat protein. Progeny bacteriophage are extruded from host bacteria (e.g., *E. coli*), and "panning" techniques that involve binding of the polypeptide of interest to a cognate binding partner are used to enrich those bacteriophage displaying the polypeptide of interest relative to other bacteriophage in the population. Smith initially reported that selection methods could be used to enrich phage displaying an EcoRI endonuclease-pIII fusion over 1000-fold. This display-and-select methodology has been extended and advanced, so that today large libraries ($>10^7$ to as many as $>10^{10}$) individual polypeptide variants may be rapidly and conveniently screened for a particular binding property of interest. See, e.g., WO 91/19818; WO 91/18989; WO 92/01047; WO 92/06204; WO 92/18619; Han et al., *Proc. Natl. Acad. Sci. USA* 92: 9747-51, 1995; Donovan et al., *J. Mol. Biol.* 196: 1-10, 1987.

Phage display often employs *E. coli* filamentous phage such as M13, fd, f1, and engineered variants thereof (e.g., fd-tet, which has a 2775-bp BglII fragment of transposon Tn10 inserted into the BamHI site of wild-type phage fd; because of its Tn10 insert, fd-tet confers tetracycline resistance on the host and can be propagated like a plasmid independently of phage function) as the displaying replicable genetic package. Considering M13 as an exemplary filamentous phage, the phage virion consists of a stretched-out loop of single-stranded DNA (ssDNA) sheathed in a tube composed of several thousand copies of the major coat protein pVIII (product of gene VIII). Four minor coat proteins are found at the tips of the virion, each present in about 4-5 copies/virion: pIII (product of gene III), pIV (product of gene IV), pVII (product of gene VII), and pIX (product of gene IX) (FIG. 1). Of these, pIII and pVIII (either full length or partial length) represent the most typical fusion protein partners for polypeptides of interest. In preferred methods of the present invention, polypeptides of interest are expressed as fusion proteins with pIX. A wide range of polypeptides, including random combinatorial amino acid libraries, randomly fragmented chromosomal DNA, cDNA pools, antibody binding domains, receptor ligands, etc., may be expressed as fusion proteins e.g., with pIII or pVIII, for selection in phage display methods. In addition, methods for the display of multichain proteins (where one of the chains is expressed as a fusion protein) are also well known in the art.

A display library is formed by introducing nucleic acids encoding exogenous polypeptides to be displayed into a phagemid vector so that a fusion protein is encoded. In preferred embodiments, the exogenous polypeptide is fused to an endogenous protein that is normally expressed on the outer surface of the phage particle.

In preferred embodiments, bacteriophage are utilized, particularly filamentous phage, and especially phage M13, fd and fl and engineered variants (i.e., versions derived from the parent bacteriophage modified using recombinant DNA methodology). Most work has inserted libraries encoding polypeptides to be displayed onto either pIII or pVIII of these phage, forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). In preferred embodiments, methods of the present invention utilize fusion proteins with pIIX of these phage. In some embodiments, a fusion protein comprises a signal sequence, usually from, but not limited to, a secreted protein other than the phage coat protein, a polypeptide to be displayed and the gene IX protein or a fragment thereof effective to display the polypeptide. The gene IX protein used for display is preferably from (i.e., homologous to) the phage type selected as the display vehicle. As described herein, exogenous coding sequences are often inserted at or near the N-terminus of gene IX although other insertion sites may be possible.

Some filamentous phage vectors have been engineered to produce a second copy of a phage gene. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation and a preferred embodiment of the present invention, exogenous polypeptide sequences are cloned into phagemid vectors which encode a phage coat protein and phage packaging sequences but which are not capable of assembling complete viral particles by itself. Phagemids are usually transformed into cells and packaged by infection with helper phage. Use of phagemid system also has the effect of diluting fusion proteins formed from coat protein and displayed polypeptide with wild-type copies of coat protein expressed from the helper phage genome. See, e.g., Garrard, WO 92/09690. In preferred methods of the present invention, wild-type copies of pIX protein may be eliminated by use of host strains that suppress expression of pIX, e.g., where suppression codons (amber, opal, and/or ochre) have been included in the wild-type (e.g., non-fused) pIX ORF.

Accordingly, in some preferred embodiments, the present invention provides vectors, systems and methods for improved phage display, especially where multivalent phage display is desired. In some preferred embodiments, the systems and methods of the present invention utilize a phagemid encoding an open reading frame comprising a pIX nucleic acid sequence operably linked to a nucleic acid sequence encoding a protein of interest. In some embodiments, the pIX nucleic acid sequences are described in detail above. In preferred embodiments, expression of this open reading frame results in production of a protein of interest-pIX fusion protein. In some preferred embodiments, this phagemid is introduced into a non-suppressor host cell strain. The present invention is not limited to the use of any particular non-suppressor host strain. Acceptable non-suppressor host strains include, but are not limited to, TOP10F'. In preferred embodiments, the phagemid is engineered to facilitate cloning of nucleic acids encoding protein of interest into the pIX gene so that a fusion protein comprising the protein of interest can be expressed. Thus, phagemids of the present invention preferably comprise a multiple cloning sites or defined cloning sites for introduction of a nucleic acid encoding a polypeptide of interest into a desired site within the coding sequence of pIX. In some embodiments, the cloning site allows expression of the polypeptide of interest at the amino terminus of pIX.

In some preferred embodiments, the phagemid is rescued with a helper phage by infecting the host strain harboring the phagemid (e.g., the non-suppressor strain) with helper phage. In some preferred embodiments, the helper phage comprises a nucleic acid comprising an open reading frame encoding M13 phage gene pIX. In preferred embodiments, this open reading frame comprises at least one non-wildtype suppressible stop codon. The present invention is not limited to the use of any particular suppressible stop codon. As non-limiting examples, the suppressible stop codons include amber, ochre, and opal stop codons. In some preferred embodiments, the non-wildtype suppressible stop codon is substituted for a wildtype codon in the pIX gene. The present invention is not limited to substitutions of suppressible stop codons at particular positions within the pIX gene. In some preferred embodiments, the non-wildtype suppressible stop codon is substituted at or following a position corresponding to wildtype amino acid three of the pIX gene.

In some preferred embodiments, the helper phage is propagated in a helper strain. In some preferred embodiments, the helper strain of the present invention is a suppressor host strain. The present invention is not limited to the use of any particular type of suppressor host strain. In some embodiments, the suppressor host strain suppresses amber, ochre, or opal stop codons. In some embodiments, the suppressor host strain has a supE, SupC or SupF genotype. Accordingly, in some embodiments, the present invention provides a suppressor host stain comprising a nucleic acid comprising an open reading frame encoding M13 phage gene pIX. In preferred embodiments, this open reading frame comprises at least one non-wildtype suppressible stop codon as described above. The suppressor host strain allows the production of infectious phage containing full length pIX.

As described above, the host strain harboring the phagemid is preferably infected with helper phage from the suppressor host strain. In preferred embodiments, following this infection, the non-suppressor host strain produces phage particles that comprise and display the pIX-POI fusion protein, but that do not comprise wild-type pIX protein.

Wildtype pIX protein is not produced by the non-suppressor host strain because the non-suppressor host strain cannot translate the suppressible stop codon in the pIX gene of the helper phage. This allows multivalent expression of the pIX-POI fusion on the phage particles.

B. Filamentous Phage

As described above, the present invention provides vectors, systems and methods for producing a filamentous phage comprising a matrix of proteins encapsulating a genome encoding a fusion protein (protein). The fusion protein comprises an exogenous polypeptide portion fused near the amino terminus of a filamentous phage pIX protein as described herein. These vectors, systems and methods utilize preferably utilize the modified pIX nucleic acids and polypeptides described in detail above.

By "exogenous" is meant that the polypeptide fused to the phage protein is not normally associated with the phage pIX protein in wild-type varieties of filamentous phage, but rather is foreign to the normal phage protein.

The filamentous phage will further contain the fusion protein displayed on the surface of the phage particle, as described herein.

Phage of some embodiments of this invention can be labeled. Preferred labels include radioactively labeled nucleic acids incorporated into the phage genome, or radioactively labeled amino acids incorporated into protein components of the phage particle. Preparation of labeled phage can be routinely prepared by growing phage as known in the art, but including radiolabeled nucleotides or radiolabeled amino acids in the culture medium for incorporation into nucleic acids or polypeptides of the phage, respectively. Exemplary labels are $^3$H-thymidine or $^{35}$S-methionine. Other isotopic labels and other nucleotide or amino acid precursors are readily available to one skilled in the art.

A filamentous phage suitable for use in some embodiments of the present invention can be any of a variety of phage particles, including both natural isolates of filamentous phage known in the art, modified filamentous phage, and artificial filamentous phage, so long as the basic properties necessary for practicing the present invention are preserved. Those properties comprise the capacity to encapsulate a genome, or a phagemid, which comprise an expression cassette that encodes the fusion protein, and the capacity to be formed into a particle which incorporates the pIX protein into the phage particle surface and display the exogenous polypeptide. The field of filamentous phage research and development has been extensive and therefore a large variety of filamentous phage variants have been described which would be suitable for use according to the present invention, including "phagemids (which by itself is not a genome)" used in preferred embodiments of the present invention, which are plasmids containing elements derived from phage genome, which in its simplest form gives them the property of being able to be encapsulated into a phage particle by use of the phage genome element when complemented with the appropriate remaining elements e.g. by helper phage rescue. Exemplary descriptions of the field of filamentous phage variants and phage genomes, the structure of filamentous phage particles, their coat proteins and particle assembly, see the reviews by Smith et al, "Phage Display" in Chem. Rev., 97:391-410, 1997; Rached et al., Microbiol. Rev., 50:401-427 (1986); and Model et al., in "The Bacteriophages: Vol. 2", R. Calendar, ed. Plenum Publishing Co., pp. 375-456, (1988).

As is noted in the field, a variety of genetic deficiencies in the wild-type filamentous phage genome can be present and complemented by the use of helper phage for production of the desired phage particle. Therefore, the invention is not to be limited to any particular phage or phagemid vector as long as the encapsulated DNA can be contained in a particle with surface expressed pIX.

C. Multivalent, Oligovalent and Monovalent Display

Fusions of a polypeptide of interest to a phage coat protein is a highly artificial system with regard to the phage, and can create problems for the artisan seeking to employ phage display methodology. For example, pIII is required for attachment of the phage to its host cell; as the polypeptide of interest increases in size, its presence on pIII hinders this normal function during early event of host infection, resulting in a loss of infectivity. As a result, contaminating phage lacking the fusion protein can out-compete the phage displaying the polypeptide of interest for infection of the host cells, reducing or even preventing successful enrichment for the polypeptide. In the case of pVIII, fusions can compromise coat protein function generally.

To overcome such difficulties at least in part, prior art methods relied on various strategies. For example, the phage genome may be introduced by electroporation rather than by reliance on natural phage infection. Alternatively, hybrid systems that contain a mixture of wild type and fusion coat protein in the same virion (e.g., "33," "3+3," "88," and "8+8" vectors) may be employed, either with (e.g., 3+3) or without (e.g., 33) the use of helper phage. Such methods may be tuned to provide "monovalent" phage display; that is, the phage particles display mostly zero or one copy of the fusion protein. While monovalent display may help to increase the selection of high affinity binding interactions, multivalent display may lead to more efficient selection. See, e.g., WO 01/40306.

In monovalent display, a preparation of phage particles prepared from *E. coli* harboring a phagemid display vector and infected with a helper phage will exhibit a Poissonian distribution of fusion proteins in which 10% or less of the particles will display one copy of the fusion protein; far less will display two copies; and the remainder will not display any copies of the fusion. Monovalent display may be utilized when the aim is to identify e.g., the most tightly bound variants from a library. However, in some cases, multivalent (also known as polyvalent) display is preferable. Multivalent display confers a high apparent avidity on weak-binding clones; however, multivalent display may be desired when an objective is to isolate rare and weakly-binding clones. In preferred embodiments of the present invention, multivalent display is enabled wherein a protein of interest is fused to pIX, and helper phage-encoded wild-type-function (e.g., non-fused) pIX protein is not present. In some embodiments, the absence of helper phage-encoded wild-type function pIX protein is facilitated through the use of suppression codons, e.g. suppressor mutations (e.g., amber, opal, and/or ochre mutations) and suppressor host strains comprising a suppressor genotype. Preferred suppressor host strains include, but are not limited to, strains with supE, SupC or SupF genotypes.

D. Phage Display Libraries

In some embodiments, methods of the present invention find use with phage display libraries. For example, the methods described herein may be used to display a variety of polypeptides, including but not limited to random combinatorial amino acid libraries, polypeptides encoded by randomly fragmented chromosomal DNA, polypeptides encoded by cDNA pools, polypeptides encoded by EST libraries, antibody binding domains, receptor ligands, and enzymes. Such polypeptides may be displayed as single chains or as multichain complexes. Libraries often have sizes of about $10^3$, $10^4$ $10^6$, $10^7$, $10^8$ or more members. The nucleic acid libraries can exist in free form, as components of any vector or as a component of a vector into host cells.

Furthermore, additional steps well known in the phage display art, such as combinatorial chain shuffling, humanization of antibody sequences, introduction of mutations, affinity maturation, use of mutator host cells, etc., may be included in the methods described herein at the discretion of the artisan. See, e.g., Aujame et al., *Hum. Antibod.* 8: 155-168, 1997; Barbas et al., *Proc. Natl. Acad. Sci. USA* 88: 7978-82, 1991; Barbas et al., *Proc. Natl. Acad. Sci. USA* 91:

3809-13, 1994; Boder et al., *Proc. Natl. Acad. Sci. USA* 97: 10701-10705, 2000; Crameri et al., *Nat. Med.* 2: 100-102, 1996; Fisch et al., *Proc. Natl. Acad. Sci. USA* 93: 7761-7766, 1996; Glaser et al., *J Immunol.* 149: 3903-3913, 1992; Irving et al., *Immunotechnology,* 2: 127-143, 1996; Kanppik et al., *J Mol. Biol.,* 296: 57-86, 2000; Low et al., *J. Mol. Biol.* 260: 359-368, 1996; Riechmann and Winter, *Proc. Natl. Acad. Sci. USA,* 97: 10068-10073, 2000; and Yang et al., *J. Mol. Biol.* 254: 392-403, 1995; each herein incorporated by reference in its entirety.

In some preferred embodiments, the present invention provides a combinatorial phage display format. In some embodiments, the protein of interest (POI) is a scFv or other antigen binding protein, a receptor, an agonist, an enzyme or other protein that binds to or otherwise interacts with another protein. In some embodiments, the present invention is used in conjunction with a filamentous phage particle encapsulating a genome encoding a fusion polypeptide, wherein the fusion polypeptide comprises a POI fused to the amino terminus of a filamentous phage pIX protein. Preferably, the phage particle comprises the expressed fusion protein on the surface of the phage particle. In some embodiments, the libraries have a combinatorial diversity of at least $10^3$, $10^4$, $10^5$, $10^6$, $10^7$, $10^8$, $10^9$, $10^{10}$, $10^{11}$, $10^{12}$, $10^{13}$, or any range or value therein, different species of POI. In some embodiments, the vector for expressing a fusion protein on the surface of a filamentous phage comprises a cassette for expressing the fusion protein. The cassette includes upstream and downstream translatable DNA sequences operatively linked via a sequence of nucleotides adapted for directional ligation of an insert DNA, i.e., a polylinker, where the upstream sequence may or may not encode a prokaryotic secretion signal, the downstream sequence encodes a pVII or pIX filamentous phage protein. The translatable DNA sequences are operatively linked to a set of DNA expression signals for expression of the translatable DNA sequences as portions of the fusion polypeptide.

In some embodiments, the suppressible helper phage of the present invention is used in conjunction with a display system for heterodimeric polypeptide arrays, such as those disclosed in WO2009/085462, incorporated by reference in its entirety. In these embodiments, a first phagemid encode a fusion polypeptide, wherein the fusion polypeptide comprises an exogenous polypeptide fused to the amino terminus of a filamentous phage pVII or pIX protein and second phagemid further encodes a second fusion polypeptide, wherein the second fusion polypeptide comprises a second exogenous polypeptide fused to the amino terminus of the pIX protein and the first exogenous polypeptide in the first fusion polypeptide is fused to the amino terminus of the pVII protein. In this embodiment, the first and second fusion polypeptides can associate to form a heterodimeric protein complex, such as an immunoglobulin Fv, a catalytic Fv, a receptor, a nucleic acid binding protein or an enzyme. In some embodiments, the vectors further comprise a second cassette (in addition to a first cassette as described above) for expressing a second fusion protein on the surface of the filamentous phage, wherein the second cassette has the structure of the first cassette with the proviso that the first fusion protein expression cassette encodes pVII protein and the second fusion protein expression cassette encodes pIX protein or vice versa. The vector is used as a phagemid to express heterodimeric protein complexes on the surface of the phage particle in which the two exogenous polypeptides of the heterodimer are anchored on the phage particle by the fusion to the first and second phage proteins, pVII and pIX, respectively.

In some embodiments, the present invention provides a library of phage particles according to the present invention, i.e., a combinatorial library, in which representative particles in the library each display a different fusion protein. Where the particle displays a heterodimeric protein complex, the library comprises a combinatorial library of heterodimers, such as antibodies in the form of a library of Fv molecules. Preferred libraries have a combinatorial diversity of at least $10^3$, $10^4$, $10^5$, $10^6$, $10^7$, $10^8$, $10^9$, $10^{10}$, $10^{11}$, $10^{12}$, $10^{13}$, or any range or value therein, different species of fusion protein.

The present invention contemplates a variety of methods for producing a combinatorial library of phage, including by cloning repertoires of genes encoding an exogenous polypeptide into a vector of the present invention, modifying the structure of the exogenous polypeptides in a library by mutagenesis, by random combination of populations of first and second fusion protein libraries, by target and affinity selection ("panning") to alter the diversity of a library, and the like.

E. Selection for Affinity to Target

Displayed library members may be enriched for polypeptides exhibiting a binding interaction of interest by screening for binding to a target. The target can be any molecule of interest for which it is desired to identify binding partners. The library members are contacted with the target, which may be labeled (e.g., with biotin) in such a manner that allows for its controlled immobilization. Binding is allowed to proceed to equilibrium and then target is brought out of solution by contacting with the solid phase in a process known as panning. Library members that remain bound to the solid phase throughout the selection process do so by virtue of bonds between them and immobilized target molecules, whereas unbound library members are washed away from the solid phase. Following washing, the target-phage bond is usually disrupted resulting in the elution of the target bound phage, hence completing the process known as panning (Parmley and Smith, *Gene* 73: 305-318, 1988).

In a variation, affinity screening to a target is performed in the presence of a compound for which binding is to be avoided (for example, a molecule that resembles but is not identical to the target). Such screening preferentially selects for library members that bind to a target epitope not present on the compound. In a further variation, bound library members can be dissociated from the solid phase in competition with a compound having known cross-reactivity with a target for an antigen. Library members having the same or similar binding specificity as the known compound relative to the target are preferentially eluted. Library members with affinity for the target through an epitope distinct from that recognized by the compound remain bound to the solid phase.

Enriched libraries produced by the above methods are characterized by a high proportion of members encoding polypeptides having specific affinity for the target. For example, at least 10, 25, 50, 75, 95, or 99% of members encode polypeptides having specific affinity for the target. The exact percentage of members having affinity for the target depends whether the library has been amplified following selection, because amplification may increase the representation of genetic deletions. However, among members with full-length polypeptide coding sequences, the proportion encoding polypeptides with specific affinity for the target may be very high (e.g., at least 50, 75, 95 or 99%). The latter is case-specific and unpredictable, and the ability to identify cognate binders will depend on the number of iterative panning cycles performed and the through-put of the downstream screening strategy employed. It is of interest to minimize the number of panning cycles to increase the diversity of the individual target-specific clones identified in downstream screening. Not all of the library members that encode a polypeptide with specific affinity for the target necessarily display the polypeptide. For example, in a library in which 95% of members with full-length coding sequences encode polypeptides with specific affinity for the target, usually fewer than half actually display the polypeptide. Usually, such libraries have at least $10^3$, $10^4$, $10^5$, $10^6$, $10^7$, $10^8$, $10^9$, $10^{10}$, $10^{11}$, $10^{12}$, $10^{13}$ different coding sequences.

EXAMPLES

The following examples are provided in order to demonstrate and further illustrate certain preferred embodiments and aspects of the present invention and are not to be construed as limiting the scope thereof.

Example 1

Incorporation of Amber Suppressor Mutations in M13K07 pIX ORF

In some embodiments of the present invention, a modified helper phage is constructed by altering the M13K07 helper phage genome (Vieira et al. (1987) Methods Enzymol. 153:3-11; herein incorporated by reference in its entirety) in the pIX ORF with the amber stop codon TAG (suppressed to Gln (Q) in supE host strains). When propagated in a suppressor *E. coli* host, full-length pIX expression is achieved resulting in near to, or normal virion assembly. When these helper phage virions are used for pIX phagemid rescue in a non-suppressor strain, such as *E. coli* TOP10F', multivalent pIX phagemid-derived display is achieved.

Since the pIX ORF does not normally include any codons for Gln, modifications in the pIX ORF are required. In some embodiments, insertion of a Gln codon occurs at a location that preserves wild-type pIX protein functionality under codon-suppressed conditions, whilst abrogation of wild-type pIX protein function occurs when the pIX ORF translation is prematurely terminated in the non-suppressor host. Since the phage genome is very compact and gene expression is tightly regulated, this insertion is made judiciously based on the following observations in the wild-type genome (FIG. 3):

1) Normal pVII translation, which is tightly coupled to upstream pV translation (Ivey-Hoyle et al. (1989) J. Mol. Biol. 208:233-244; herein incorporated by reference in its entirety), is required for downstream pIX translation, hence wild-type pVII functionality is preferably preserved (Blumer et al. (1987) J. Mol. Biol. 197:439-451; herein incorporated by reference in its entirety).

2) The pVII ORF terminates internally in the 5'-portion of the pIX ORF, hence no modifications are made in the first, or the two first amino acids (aa) of the pIX ORF.

3) The pIX ORF terminates internally in the 5'-portion of the pVIII ORF. Moreover, pVIII has its translational initiation site (Shine Dalgarno sequence) in the 3'-portion of the pIX ORF (Blumer et al. (1987) J. Mol. Biol. 197:439-451; herein incorporated by reference in its entirety). Hence, to preserve wt pVIII functionality, no modifications are made in the eight last aa of the pIX ORF.

Prior to virion incorporation, pIX is found as a transmembrane protein in the inner membrane of the gram negative host (Endemann et al. (1995) J. Mol. Biol. 250:496-506; herein incorporated by reference in its entirety), where it together with pVII initiates virion assembly by interacting with the newly replicated phage RF DNA. The membrane orientation of pIX is such that the amino-terminus is exposed to the periplasm, whereas the carboxy-terminus is exposed to the cytosol (Simons et al. (1981) PNAS 78:4194-4198; Houbiers et al. (1999) Biochem. 38:1128-1135; each herein incorporated by reference in its entirety). Upon virion assembly, the carboxy-terminus is embedded into the virion (Endemann et al. (1995) J. Mol. Biol. 250:496-506; herein incorporated by reference in its entirety). pIX does therefore not tolerate any carboxy-terminal modifications, whereas minor amino-terminal modifications are readily tolerated (Gao et al. (1999) PNAS 96:6025-6030; herein incorporated by reference in its entirety).

Therefore, to preserve wild-type pIX functionality (e.g., membrane/capsid insertion, ssDNA virion incorporation, normal pVII/pVIII translation) upon full-length translation and at the same time most effectively knocking down functionality in the non-suppressor host, any modifications are done immediately downstream of the two 5'-encoded amino acids in the pIX ORF. It is beneficial to incorporate more than one amber stop codon to completely knock down pIX translation in the non-suppressor host (Baek et al. (2002) Nucleic Acids Res. 30:e18; herein incorporated by reference in its entirety). More precisely, the wild-type pIX amino acid sequence is modified from:

(SEQ ID NO. 1)
N-MSVLVYSFASFVLGWCLRSGITYFTRLMETSS-C (SEQ ID NO. 2)
ATGAGTGTTTTAGTGTATTCTTTCGCCTCTTTCGTTTTAGGTTGGTGCCT
TCGTAGTGGCATTACGTATTTTACCCGTTTAATGGAAACTTCCTCATGA to:

(SEQ ID NO. 3)
N-MSQ$^{amber}$XQ$^{amber}$VLVYSFASFVLGWCLRSGITYFTRLMETSS-C, (SEQ ID NO. 4)
ATGAGTTAGXTAGGTTTTAGTGTATTCTTTCGCCTCTTTCGTTTTAGGTT
GGTGCCTTCGTAGTGGCATTACGTATTTTACCCGTTTAATGGAAACTTCC
TCATGA where X denotes any residue and Q$^{amber}$ is encoded by the codon 5'-TAG-3'. As amber suppression is most effective if immediately preceded by a purine nucleotide (Bossi et al. (1983) J. Mol. Biol. 164:73-87; herein incorporated by reference in its entirety), the X codon should therefore be based on such a codon. Preferably, the X residue is a small amino acid (to minimize the risk of any interference), such as Ser (e.g., as encoded by codon 5'-AGC-3'), or Gly (e.g., as encoded by codon 5'-GGA-3'). In the example described herein, the X residue was chosen to be Ser using the codon 5'-AGC-3' (FIG. 3).

Alternatively, the pIX ORF (location of the modification as shown in SEQ ID NO: 2) is modified by inserting one or more amber stop codons by substituting one or more amino acids of the native pIX sequence with an amber stop codon, such that the total number of amino acids in the modified and native pIX is identical.

Methods
Reagents

All media and buffers were prepared essentially as described in Sambrook et al. (2001) Molecular Cloning: A Laboratory Manual. Cold Spring Harbor, N.Y.: Cold Spring Harbor Laboratory Press. Restriction enzymes (RE) and T4 DNA ligase were purchased from New England Biolabs (Ipswich, Mass., USA). DNA oligos were purchased from Eurofins MWG Operon (Ebersberg, Germany). Pfu Turbo DNA and Phusion DNA polymerases were purchased from Stratagene (LaJolla, Calif., USA) and Sigma-Aldrich (Oslo, Norway), respectively.

Helper Phages and Bacterial Strains

M13K07 helper phage was purchased from GE Healthcare Bio-Sciences AB (Uppsala, Sweden). VCSM13 helper phage and *E. coli* XL1-Blue (recA1 endA1 gyrA96 thi-1 hsdR17 supE44 relA1 lac [F' proAB lacI$^q$ZΔM15 Tn10 (Tet$^r$)]) was purchased from Stratagene (LaJolla, Calif., USA). *E. coli* MC1061 (hsdR mcrB araD139 Δ(araABC-leu)7679 Δ(lac)174 galU galK strA thi) was a kind gift from Dr. G. P. Smith (Division of Biological Sciences, University of Missouri, USA) and *E. coli* TOP10F' (mcrA Δ(mrr-ladRMS-mcrBC) Φ80lacZΔM15 ΔlacX74 recA1 araD139 Δ(ara leu) 7697 galU galK rpsL (Str$^r$) endA1 nupG F'[lacI$^q$, Tn10 (Tet$^r$)]) was obtained from Life Technologies (UK).

Design and In Vitro Mutagenesis of pIX$^{Amber}$

The pIX ORF was modified as shown in FIG. 3 by QuikChange™ in vitro mutagenesis according to the manufacturers' protocol (Stratagene, LaJolla, Calif., USA), using the primer pair pIX_amber_F/pIX_amber_R (5'-GCTGGGGGTCAAAGATGAGTTAGAGCTAGGTTTTAGTGTATTCTT

TCGC-'3/5'-GCGAAAGAATACACTAAAACCTAGCTCTAACTCATCTT

TGACCCCCAGC-3')(SEQ ID NO: 5 and SEQ ID NO: 6, respectively), and introduced into *E. coli* MC1061 by electroporation. Primer design was based on the sequence of VCSM3 (GenBank accession no.: AY598820) (SEQ ID NO:7). Successful introduction of the mutation was verified by DNA sequencing (in-house ABI lab DNA sequencing core facility, Dept. Molecular Biosciences, University of Oslo). To ensure a clean vector background, a BsrGI/SnaBI RE fragment containing the modified pIX was moved into either the M13K07 or VCSM13 genome on the compatible BsrGI/SnaBI RE sites (FIG. 3) using standard techniques. The DNA constructs were subsequently introduced into the *E. coli* XL1-Blue by heat shock.

Preparation of Phage Particles

Phages were amplified from *E. coli* XL1-Blue transformed with the M13K07, or the pIX$^{Amber}$ genomes essentially as described (Scott and Smith, PMID: 1696028). *E. coli* proliferation was measured at $A_{600\ nm}$. Virion assembly was monitored by spot titration as described (Koch et al, PMID: 11126120). The *E. coli* XL1-Blue derived phage preparations of M13K07 and the pIX$^{Amber}$ mutant was used to transducer *E. coli* TOP10F' using standard methodology. Phages were then amplified from *E. coli* TOP10F' as described above.

Results

Figures 3A, 3B:
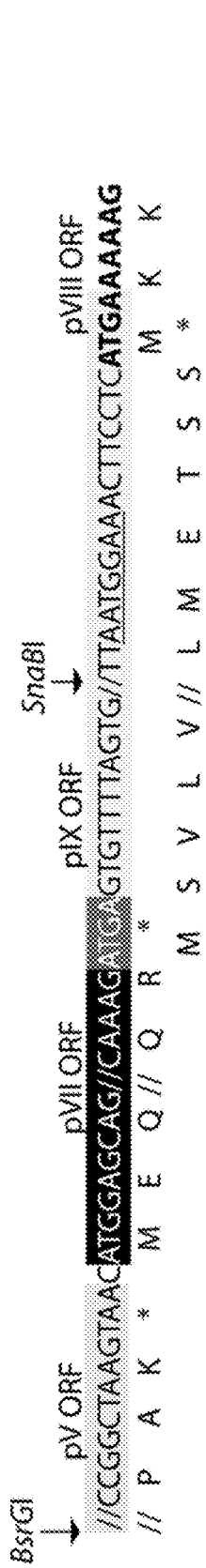
FIG. 3A-B Illustration of the genomic Ff region with sequences important for the pIX$^{Amber}$ mutant design. The wild type region as found in the M13K07, VCSM13 and fd genomes (A, SEQ ID NOs: 8 (nucleic acid) and 9 (amino acid)) and modified with the pX$^{Amber}$ mutations (B, SEQ ID NOs:10 (nucleic acid) and 11 (amino acid)). Only partial sequences are shown and the identity of the open reading frames (ORF) are given above the DNA sequences with corresponding shading of the DNA sequences. The translated ORFs are given below the DNA sequence and the pVIII translation initiation site is indicated in underline within the pIX ORF. The conserved BsrGI and SnaBI restriction enzyme sites are arbitrarily placed to indicate the relative position.
Figure 4A:
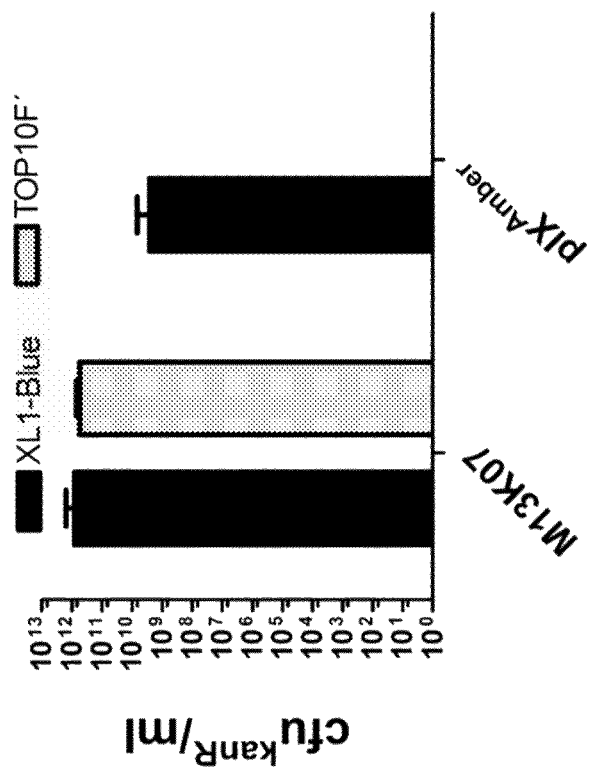
FIG. 4A-B Single colonies of either *E. coli* XL1-Blue or TOP10F' were grown over night in selective medium before the end cell density was measured at $A_{600\ nm}$ (A). The virion content in the cultures from A was determined by infectious titration and the result given as kanamycin-resistant colony forming units (cfu$^{kamR}$) per ml (B).
Figure 4B:
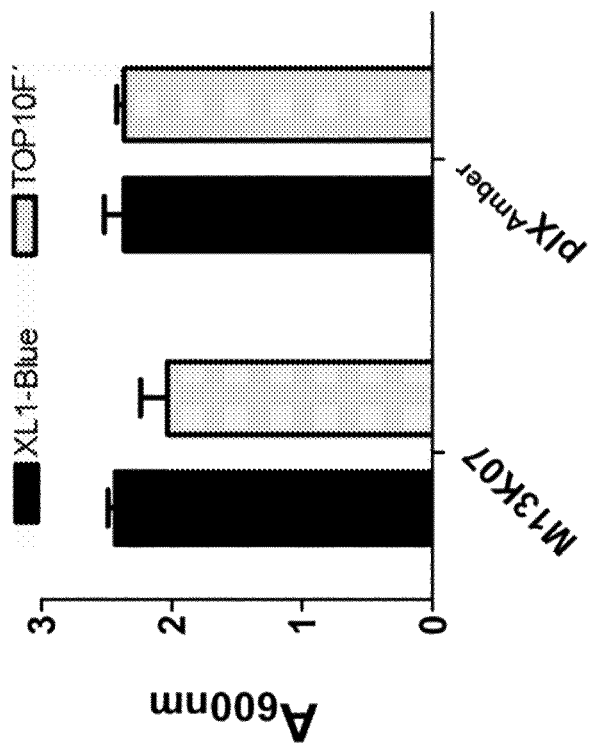

The pIX$^{Amber}$ mutant was designed and constructed based on M13K07 and the functionally identical VCSM13, as described in methods and shown in FIG. 3. Notably, the M13K07 and VCSM13 genomes are identical in the region we introduced the mutations (data not shown). The amber mutations should only affect virion assembly depending on the suppressor genotype of the producing host and not the genome propagation which confer kanamycin resistance to the propagating host. We therefore tested this notion by growing both *E. coli* XL1-Blue (supE positive) and TOP10F' harbouring either M13K07 or the M13K07 pIX$^{Amber}$ mutant as ON cultures under identical conditions. In all cases, similar cell densities at plateau levels were reached, showing that the M13K07 control and the M13K07 pIX$^{Amber}$ mutant perform identical with respect to host proliferation (FIG. 4A). A control culture not harboring the phage genomes did not grow due to lack of kanamycin resistance (data not shown). The virion production capacity of the cultures was assess by infectious titration based on transduction of fresh host cells as described. Whereas the M13K07 control reached normal titers (given as kanamycin resistant colony forming units per ml (cfu$^{kanR}$/ml)) in both XL1-Blue and TOP10F', no virions were produced from the supE-negative TOP10F' harbouring the pIX$^{Amber}$ mutant (FIG. 4B). The latter showed that our introduced amber mutations resulted in the intended phenotype, namely a complete abrogation of virion production due to lack of functional pIX expression, which is an absolute requirement for virion assembly (Endemann and Model, PMID: 7616570). Contrary, high titers of the pIX$^{Amber}$ mutant was obtained from the supE-positive XL1-Blue, though a mild reduction as compared to the M13K07 control was observed (FIG. 4B). The mild reduction in titer seen with the pIX$^{Amber}$ mutant is of no practical issue, as high titer concentrate equal to the M13K07 control is easily obtainable by a slight up-scale of the culture volume in combination with PEG precipitation of the particles. The reduction in titer does however imply that the pIX$^{Amber}$ modification has a direct influence on the virion producing capacity, which has been observed, and most often to a larger degree, with mutant helper phages (Bradbury et al. (2004) J. Immunol. Meth. 290:29-49; herein incorporated by reference in its entirety).

Example 2

Incorporation of Opal or Ochre Suppressor Mutations in M13K07 pIX ORF

The pIX ORF (location of the modification as shown in SEQ ID NO: 2) may also be modified by inserting either an opal stop codon (i.e., resulting in creation of "TGA" codon; also referred to as umber mutation) (Miller et al. (1983) J. Mol. Biol. 164:59-71; herein incorporated by reference in its entirety) or ochre stop codon (i.e., resulting in the creation of "TAG" or "TAA" codons). In some embodiments, such modifications do not require any amino acid insertions in the pIX ORF. This approach, however, requires the use of a different suppressor host than those based on the supE genotype (such as *E. coli* XL1-Blue, TG1, etc). In one non-limiting example, an opal suppressing strain, ISM612, has been described (Minion et al. (20060 FEMS Microbiol. Lett. 131:81-85; herein incorporated by reference in its entirety).

Example 3

Permanent Suppression of M13K07 pIX ORF and Complementation with Exogenous pIX

In some embodiments, the pIX ORF is permanently destroyed by either inserting one or more non-suppressible stop codons (in relation to the chosen *E. coli* host) in the region not interfering with pVII and pVIII translation, or performing a deletion of the encoding DNA in this region. Such a deletion is preferably designed according to the criteria described Example 1 delineating the gene regulation observed in the wild-type genome. Two criteria that limit the size of the deletion are the necessity of pVII translation stop and the preservation of the pVIII translation initiation site (underlined in FIG. 3). Thus, the largest deletion affecting only pIX encompasses the region from the second nucleotide in the second codon of the pIX ORF to the first nucleotide in the sixth last amino acid encoding codon of the pIX ORF (FIG. 3A). Any smaller deletion within these boundaries will hence result in the same effect as this large deletion. Notably, smaller deletions within these boundaries, such as single amino acid deletions, may be tolerated without compromising the pIX function, but then no pIX knock-down is achieved. Alternatively, the normal pVIII translation initiation may also be sacrificed and substituted with the original pIX reading frame by deleting the region from the first nucleotide in the second codon of the pIX ORF to the last nucleotide in the first codon of the pVIII ORF (FIG. 3A). In either case, it is necessary to produce viable, infectious helper phage virions by complementing pIX from an exogenous source. Two non-limiting strategies for providing pIX include:

1) Constructing a dedicated host cell packaging line by performing a genomic knock-in of a functional pIX expression cassette in an appropriate *E. coli* host strain, e.g. as described for the DH5α/pIII packaging line for HyperPhage (Rondot et al. (2001) Nature Biotechnol. 19:75-78; Diederich et al. (1992) Plasmid 28:14-24; each herein incorporated by reference in its entirety), and 2) Constructing a helper plasmid containing a pIX expression cassette. This plasmid is then co-propagated in the same *E. coli* host together the pIX ORF-compromised helper phage genome, resulting in normal virion assembly. Such a system is analogous to that described, e.g., for manufacturing pIII modified helper phages (Kramer et al. (2003) Nucleic Acids Res. 31:e59; Chasteen et al. (2006) Nucleic Acids Res. 34:e145; each herein incorporated by reference in its entirety).

Example 4

The Use of the M13K07 pIX$^{Amber}$ Mutant Helper Phage for Multivalent Phagemid Display The M13K07 pIX$^{Amber}$ mutant described in Example 1 was designed to have conditional pIX expression depending on the host suppressor genotype. This allows for propagation of the helper phage genome and production of helper phage virions when using a supE positive host. The resulting helper phage virions can then be used for standard phagemid rescue (Bradbury et al. (2004) J. Immunol. Meth. 290:29-49; herein incorporated by reference in its entirety). In some embodiments of the invention, the phagemid in question is designed for pIX display of a heterologous peptide. Depending on the genotype of the *E. coli* host from which the phagemid is rescued, there will be either one or two sources of functional pIX for new virion assembly, namely the phagemid (with the heterologous peptide fusion) and the helper phage genome, or only the phagemid. In the former case, which depends on a supE positive host such as *E. coli* XL1-Blue, the resulting virions will display a mixture of phagemid and helper phage derived pIX, resulting in mono- to oligovalent display of the heterologous fusion (FIG. 2B). In the latter case, which depends on a supE negative host such as *E. coli* TOP10F', the resulting virions are forced to incorporate phagemid-derived pIX only, resulting in multivalent display of the heterologous fusion (FIG. 2C).

When comparing low valence display (mono- to oligovalent) with multivalent display, a markedly increased antigen (Ag) reactivity should be obtained with the multivalent display virions due to functional affinity effects (also called avidity) as stated by Karush (PMID: 4905692). As outlined by Crothers and Metzger functional affinity does not follow the law of mass action (Crothers and Metzger, 1972, PMID: 4113719). Thus, the gain in binding strength of a particular multivalent POI to its target due to avidity (as compared to its monovalent counterpart) will vary with the both the experimental condition (such as reaction volume and target density) and with the valence and the functional connector between the binding sites of the multivalent POI (Crothers and Metzger, 1972, PMID: 4113719 and Mattes, 1995, PMID: 7493337). Nonetheless, in direct comparisons between low and high valence display in affinity selection using phage display, multivalent display has proven superior in facilitating discovery of new POI specificities towards defined targets (O'Connell et al. (321) J. Mol. Biol. 321:49-56; herein incorporated by reference in its entirety).

Initially it had been found that attempts at phage assembly in the absence of pIX almost completely abolish the production of phage. In addition, initial attempts at displaying a fusion protein on pIX suggested that pIX was not functional when fused with another protein at its N-terminus (Endemann et al, J. Mol. Biol., 250:496-506, 1995), suggesting that display would not be feasible using pIX. However, subsequent work has proven the feasibility of using pIX for fusion proteins in phage display (Gao et al., 1990, PMID: 10339535; herein incorporated by reference in their entirety). The critical parameter for achieving pIX display was the inclusion of a signal sequence to target the recombinant POI-pIX fusion to the periplasm in combination with wild type pIX complementation from the helper phage to preserve the pIX functionality essential for virion assembly (Gao et al., 1990, PMID: 10339535; herein incorporated by reference in their entirety). Later, it has been shown that the signal sequence is of less importance (WO 2010/097411; herein incorporated by reference in its entirety). It is therefore unknown whether or not it is possible to produce virions where all pIX copies harbor a fusion. By exploiting the M13K07 pIX$^{Amber}$ mutant described in Example 1 for phagemid rescue of pIX display phagemids using a supE negative host cell would therefore allow us to test if it is possible to achieve multivalent pIX display. If such virions are assembled, they should then exhibit increased target reactivity as compared to their low valence display counter parts.

Methods

Reagents

All media and buffers were prepared essentially as described in Sambrook et al. (2001) Molecular Cloning: A Laboratory Manual. Cold Spring Harbor, N.Y.: Cold Spring Harbor Laboratory Press. The anti-M13-HRP antibody was purchased from GE Healthcare Bio-Sciences AB (Uppsala, Sweden). Bovine serum albumin (BSA) and Tween 20 was purchased from Sigma-Aldrich (Oslo, Norway). The haptens 2-phenyloxazol-5-one (phOx) and 5-nitrophenacetyl (NIP) conjugated to BSA were prepared essentially as described elsewhere (Naikelai et al, PMID; 722243 and Michaelsen et al, PMID: 2125362). The *E. coli* strain XL1-Blue was purchased from Stratagene (LaJolla, Calif., USA). M13K07 helper phage was purchased from GE Healthcare Bio-Sciences AB (Uppsala, Sweden) whereas *E. coli* XL1-Blue (recA1 endA1 gyrA96 thi-1 hsdR17 supE44 relA1 lac [F' proAB lacI$^q$ZΔM15 Tn10 (Tet$^r$)]) and TOP10F' (mcrA Δ(mrr-hsdRMS-mcrBC) Φ80lacZΔM15 ΔlacX74 recA1 araD139 Δ(ara leu) 7697 galU galK rpsL (Str$^r$) endA1 nupG F'[lacI$^q$, Tn10 (Tet$^r$)]) was purchased from Stratagene (LaJolla, Calif., USA) and Life Technologies (UK), respectively. All pIX display phagemids used herein have been described in detail in WO 2010/097411(herein incorporated by reference in its entirety).

Preparation of Phage Particles

Helper phage rescue of phagemids either from *E. coli* XL1-Blue, or TOP10F' was done as described (Welschof et al, PMID: 9050877). Virions were purified from 50 raw supernatant and concentrated to 1 ml by PEG/NaCl precipitation as described (Welschof et al, PMID: 9050877). Virion assembly was monitored by spot titration as described (Koch et al, PMID: 11126120).

Phage-Capture Enzyme Linked Immunosorbent Assays (ELISAs)

phOx-BSA was absorbed to MaxiSorp™ microtiter plate wells (Nunc, Roskilde, Denmark) at 5 µg/ml in PBS, pH 7.4 overnight at 4° C. The wells were blocked with 2% BSA in PBS (w/v) for 1 h at RT, virion preparations where then added and allowed to react for 1.5 at room temperature (RT) before captured virions were detected with anti-M13-HRP (1:3,000) for 1 h at RT. Between each step, the wells were washed 3× with PBST (PBS/0.05% Tween 20). The wells were developed with TMB soluble substrate, stopped with 1M HCl after 30 min and the absorbance read at $A_{450\ nm}$.

SDS PAGE and Western Blotting

The display level of the pIX fusions was investigated by SDS-PAGE and western blotting as follows. About $10^8$ $cfu^{ampR}$ phages/sample were separated on a 14% Bis-Tris XT Precast gel (Bio-Rad, Hercules, Calif., USA), followed by electroblotting onto a polyvinylidine fluoride membrane (Millipore, Madison, USA) in Tris/glycine buffer (25 mM Tris, 192 mM glycine, 20% methanol, pH 8.3) at 25 V for 30 min using a semi-dry blotting apparatus (Bio-Rad, Hercules, Calif., USA). The membrane was blocked in PBS™ (PBS containing 0.05% v/v Tween 20 and 4% w/v skim milk) for 1 h at RT. The membrane was flushed once in PBST before incubated with rabbit anti-human X L-chain Ab (Dako) at 1:5000 in PBS™ for 1 h at RT. The membrane was washed three times in PBST followed by incubation with donkey anti-rabbit IgG HRP Ab (Amersham) at 1:10 000 in PBS™ for 1 h at RT. The membrane was washed three times in PBST and once in PBS and developed with SuperSignal West Pico Chemiluminescent Substrate (Pierce, Rockford, Ill., USA) and visualized on BioMax MR film (Kodak, Femwald, Germany).

Results

As outlined above, the first notion to test was whether or not the M13K07 pIX$^{Amber}$ mutant described in Example 1 allowed phagemid rescue of pIX display phagemids. Four different pIX display phagemids were tested and rescue was done both from the supE positive *E. coli* XL1-Blue and the supE negative TOP10F'. Normal M13K07 helper phage was used in parallel as control. The phagemids encode two different antibody derived fragments in the form of single chain Fvs (scFv), either specific for the hapten phOx or NIP when conjugated to bovine serum albumin (BSA). Moreover, the scFv-pIX fusions are found in two different forms, either with or without (denoted ΔL) a signal sequence targeting the fusion protein to the periplasm of the producing host. All four phagemids have been described in detail previously (WO 2010/097411).

Figure 5B:
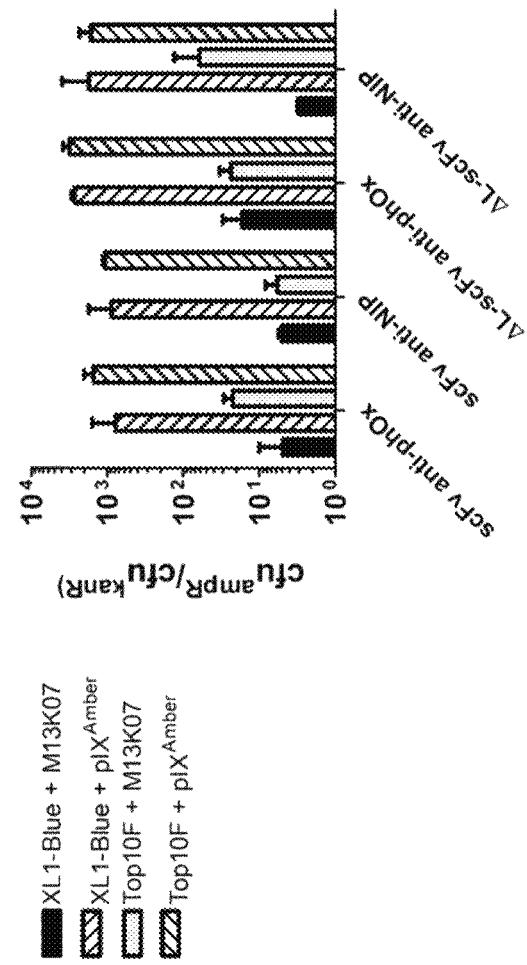
FIG. 5A-B Four different pIX display phagemids encoding two different scFv-pIX variants (with, or without a periplasmic signal sequence (ΔL) were rescued from both *E. coli* XL1-Blue and TOP10F', using either the M13K07 pIX$^{Amber}$ mutant helper phage (pIX$^{Amber}$), or the M13K07 control. End titer of phagemid virions was determined by infectious titration and the result given as ampicillin-resistant colony forming units (cfu$^{ampR}$) per ml (B). The phagemid to helper phage ratios was determined by infectious titration and selective growth on either ampicillin or kanamycin. The ratio is given as Cfu$^{ampR}$/cfu$^{kamR}$.
Figure 5A:
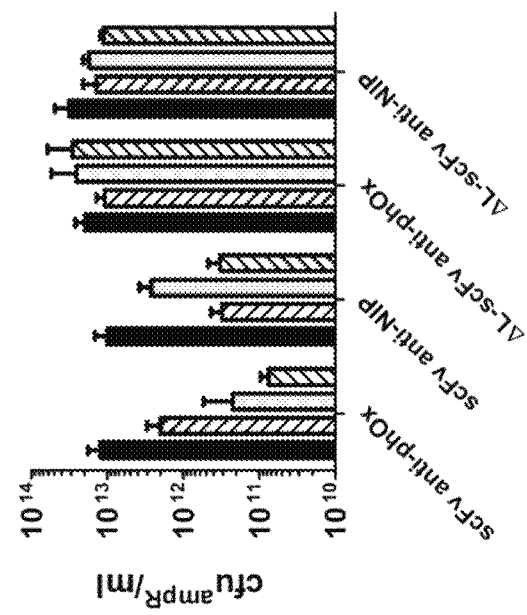

Using a standard phagemid rescue protocol the results showed that virions were produced in all cases (FIG. 5A). Surprisingly, there was a marked difference between the titers obtained for the signal sequence containing scFv as compared with their signal sequence-lacking counterparts. Whereas the signal sequence-lacking scFvs reached similar and very high end titer brushing the border of phage solubility, the signal sequence-containing counterparts both produced less virion in TOP10F' than in XL1-Blue and less virion when rescued with the M13K07 pIX$^{Amber}$ mutant as compared to the M13K07 control (FIG. 5A). The difference in end titer due to different producing host is independent of the present invention as this was seen also with the M13K07 control and can be attributed to unknown phenotype traits inherently different between these two *E. coli* strains. It is therefore both surprising and interesting that this difference was not seen using the signal sequence-lacking scFvs and high end titer is desirable if achievable. Nonetheless, all samples reach end titer sufficiently high to make then fully capable of performing efficient library selection.

In all phagemid-based systems there are two sources of ssDNA that can be encapsulated in the virion upon phagemid rescue, namely the phagemid and the helper phage genome. Phage display technology is critically dependent upon a physical coupling between the phenotype (which is displayed on the virion surface) and the corresponding genotype (which is encapsulated within the very same virion that display the fusion) (Bradbury et al. (2004) J. Immunol. Meth. 290:29-49; herein incorporated by reference in its entirety). It is therefore important to control that it is the phagemid that is preferentially packaged within the virions and not the helper phage. As both the phagemid and the helper phage harbor selectable antibiotic markers that differ, this can be conveniently checked by counting the ampicillin (on the phagemid) and the kanamycin (on the helper phage genome) resistant colony forming units (cfu) from a given sample during infectious titration (Koch et al, PMID: 11126120). By dividing the resulting $cfu^{ampR}$ on the $cfu^{kanR}$, this yield a ratio, which if is above 1 (100) indicates that the phagemid is preferentially packaged as it should. The larger the ratio, the stronger is the phenotype to genotype coupling, which is highly desirable and which becomes increasingly important with increasing library size, a weak phenotype to genotype coupling may result in loss of the clone during affinity selection. We therefore determined the phagemid to helper phage ratios of the rescued samples in FIG. 5A based on the corresponding titers. All samples exhibited ratios above 1, but to our surprise, the ratios from all the samples rescued with M13K07 pIX$^{Amber}$ mutant showed a tremendous increase in this value as compared to the corresponding sample rescued with the M13K07 control (FIG. 5B). This effect was highly significant and independent on the cell type producing the virion.

Figure 6A:
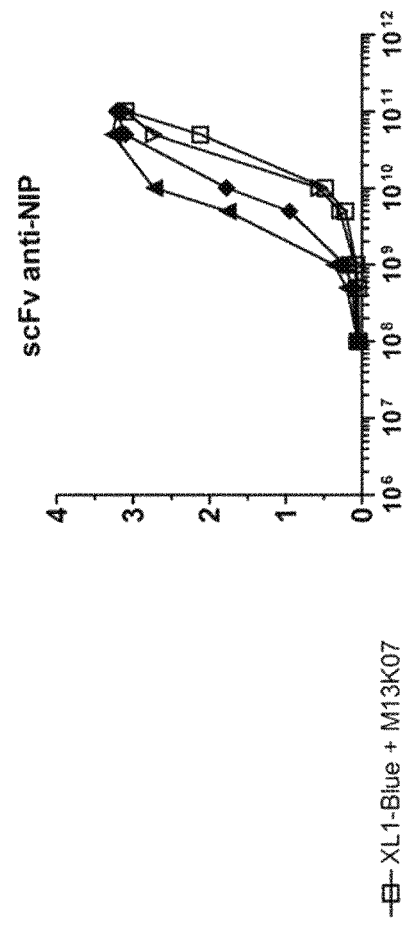
FIG. 6A-D Ag-specific phage capture ELISA. Serial dilutions of the various phage samples were tested to binding to a constant amount of Ag (either phOx-BSA, or NIP-BSA). The virions were detected with an anti-M13-HRP antibody.
Figure 6B:
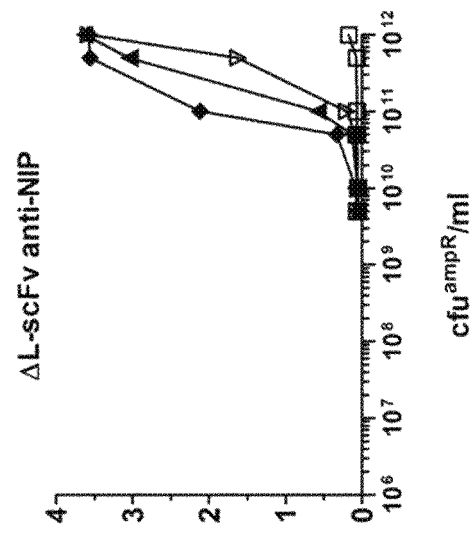
Figure 6C:
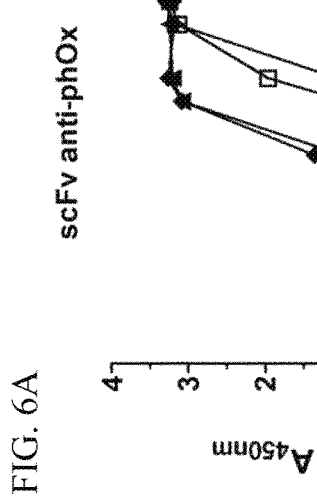
Figure 6D:
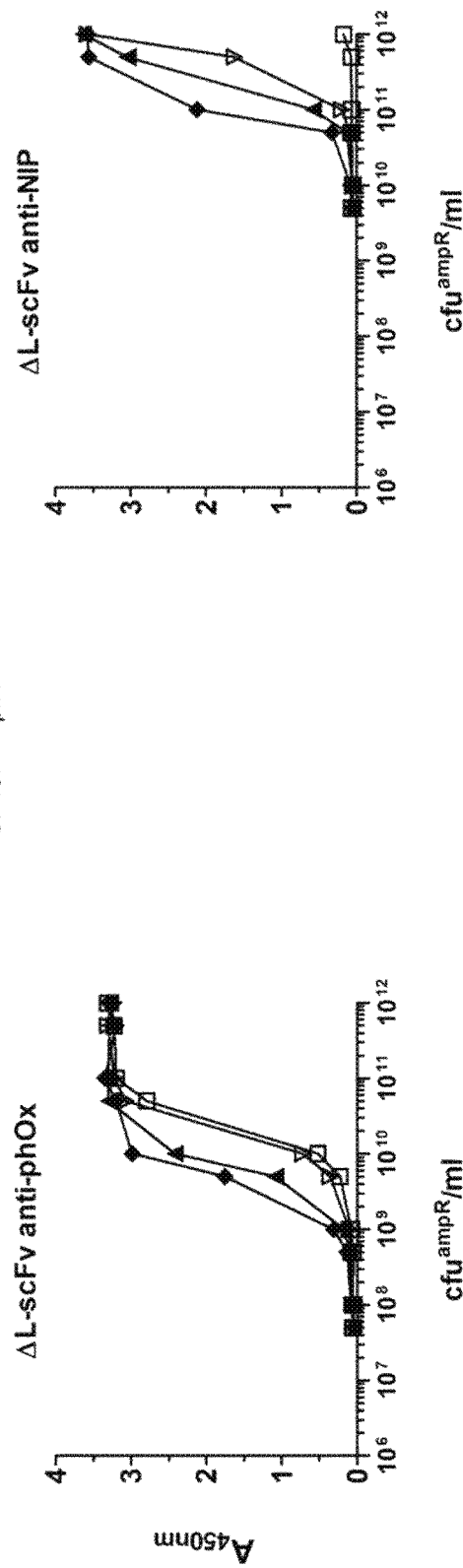

Next, we tested the produced virions for Ag reactivity as normalized serial dilutions of the samples in a phage capture ELISA. A significant increase in Ag reactivity from the M13K07 pIX$^{Amber}$ mutant rescued samples as compared with those rescued with the M13K07 control was indeed seen (FIG. 6). This was true for both the signal sequence containing (FIGS. 6A and B) and lacking (FIGS. 6C and D) scFv variants. As previously described, there is an inherent difference in Ag reactivity between the signal sequence containing and lacking scFv variants, such that the latter exhibits somewhat weaker reactivity (WO 2010/097411). This finding is confirmed here (comparing A and C, and B and D). This effect varies depending on the particular POI displayed and the strongest effect of using the M13K07 pIX$^{Amber}$ mutant as compared to the normal M13K07 helper phage is seen in FIG. 6D applied with the poorly expressed scFv anti-NIP (WO 2010/097411). Here, the standard system using XL1-Blue and M13K07 render nearly Ag nonreactive virions, which is in gross contrast to the result when using the M13K07 pIX$^{Amber}$ mutant in combination with TOP10F' (FIG. 6D). It is noteworthy that, as with the virion producing capacity, the Ag reactivity also depends on the producing host cell independent on the helper phage system used. This host cell effect is also not consistent, as the XL1-Blue performs best with the scFv anti-phOx (FIG. 6A), whereas the situation is reversed with the ΔL-scFv anti-NIP (FIG. 6D). Importantly, and as part of the current invention, the M13K07 pIX$^{Amber}$ mutant always resulted in virions exhibiting superior Ag reactivity as compared with those rescued with the M13K07 control.

Figure 7:
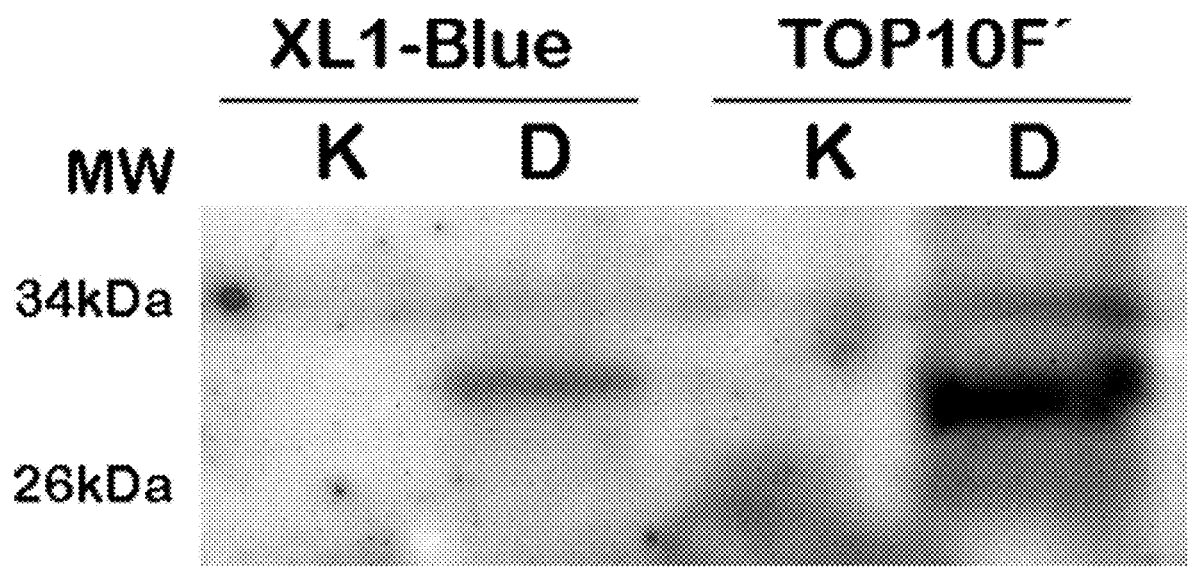
FIG. 7 Western blot analysis of the scFv anti-phOx samples prepared either in *E. coli* XL1-Blue or TOP10F', and rescued either with the M13K07 helper phage control (K), or the M13K07 pIX$^{Amber}$ mutant (D). Equal amounts (108 cfu$^{ampR}$) of virions were separated by 14% denaturing SDS PAGE, blotted onto a PDVF membrane and the scFv fusion detected with an anti-human L chain antibody.

M13K07 pIX$^{Amber}$ mutant helper phage was designed to yield multivalent display when use for phagemid rescue in a supE negative host, such as E. coli TOP10F'. To be able to produce the helper phage virion, a supE positive host such as E. coli XL1-Blue is preferably used (Example 1). It was therefore a bit surprising that the use of the M13K07 pIX$^{Amber}$ mutant helper phage for phagemid rescue in combination with E. coli XL1-Blue yielded virions with stronger Ag reactivity than when rescued with the M13K07 control. In some instances, this effect was clone dependent (FIG. 6A vs B) and for one particular clone (scFv anti-phOx), there was no difference between the host cell line, but merely between which helper phage used (FIG. 6A). As the M13K07 pIX$^{Amber}$ mutant helper phage is produced in supE positive E. coli XL1-Blue, but not in the supE negative E. coli TOP10F', helper phage derived pIX should dilute the phagemid derived POI-pIX fusion from the phagemid when using E. coli XL1-Blue. In standard systems such as E. coli XL1-Blue in combination with M13K07 this results in primarily monovalent display and only 1-10% of the total virions carry the fusion at all (Bradbury et al. (2004) J. Immunol. Meth. 290:29-49; herein incorporated by reference in its entirety). It therefore seems like the M13K07 pIX$^{Amber}$ mutant helper phage results in either oligovalent display (FIG. 2B) and/or increasing the amount of virions harboring the fusion (which would be highly desirable as it would increase the functional fraction of a library). In either case, increased Ag-reactivity will be observed (as seen in FIG. 6). This effect was completely unforeseen as it is known that normally pIX is produced in large excess in the cytosol of the producing host (Endemann et al, J. Mol. Biol., 250:496-506, 1995), but must be assigned to lowered pIX$^{Amber}$ levels as compared to pIX$^{wt}$, resulting in increased amount of POI-pIX fusion in the samples. To test this notion, we therefore separated equal amounts of purified virions by SDS PAGE and detected the fusion by western blotting. Whereas the samples rescued with the M13K07 control contained fusion levels outside the detection level, there was indeed an increased amount of fusions present in the samples rescued with the M13K07 pIX$^{Amber}$ mutant helper phage (FIG. 7). In line with the aspects discussed above, the amount of fusion was greater in the samples rescued from E. coli TOP10F' (where no helper phage pIX complementation can occur) than with the samples rescued from XL1-Blue.

In conclusion, the current examples show that the novel M13K07 pIX$^{Amber}$ mutant helper phage described herein allows for efficient pIX display phagemid rescue, resulting in multivalent display of the POI-pIX fusion that translates into markedly increase Ag-reactivity, as compared with its low valence counterpart, due to avidity effects.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, virology, phage genetics, bacteriology, or related fields are intended to be within the scope of the following claims.

The invention claimed is:

1. A nucleic acid expressible in a non-suppressor host strain, said nucleic acid comprising an open reading frame encoding phage gene pIX, wherein said open reading frame comprises at least one non-wildtype suppressible stop codon located between the first two N-terminal amino acids and the last eight C-terminal amino acids in the pIX open reading frame and wherein when expressed in said non-suppressor host strain all copies of wild-type pIX are replaced by said protein of interest-pIX fusion protein.

2. The nucleic acid of claim 1, wherein phage is selected from the group consisting of M13, fd and fl phages.

3. The nucleic acid of claim 1, wherein said at least one non-wildtype suppressible stop codon is selected from the group consisting of amber, ochre, and opal stop codons.

4. The nucleic acid of claim 1, wherein said nucleic acid encodes an amino acid sequence at least 50% identical to SEQ ID NO:3, with the proviso that said open reading frame includes at least one non-wildtype suppressible stop codon.

5. A vector comprising the nucleic acid sequence of claim 1.

6. A phage comprising the nucleic acid sequence of claim 1.

7. A system for phage display comprising:
a) a phagemid capable of modification by inclusion of a nucleotide sequence encoding a protein of interest, said nucleotide sequence operably linked to an open reading frame encoding M13 phage pIX; and
b) a phage comprising the nucleic acid sequence of claim 1.

8. The system of claim 7, further comprising a suppressor host strain.

9. The system of claim 7, wherein said suppressor host strain is selected from the group consisting of strains having a supE, SupC or SupF genotype.

10. The system of claim 7, further comprising a non-suppressor host strain.

11. The system of claim 10, wherein said non-suppressor host strain is selected from the group consisting of MC1061, HB2151, ER2738, JM101, DH5αF and TOP10F'.

* * * * *

UNITED STATES PATENT AND TRADEMARK OFFICE
CERTIFICATE OF CORRECTION

PATENT NO. : 10,640,761 B2
APPLICATION NO. : 15/406196
DATED : May 5, 2020
INVENTOR(S) : Geir Age Loset and Inger Sandlie Page 1 of 1

It is certified that error appears in the above-identified patent and that said Letters Patent is hereby corrected as shown below:

In Claim 2, Column 43, Line 41, "from the group consisting of M13, fd and fl phages." should read -- from the group consisting of M13, fd and fl phages. --.

Signed and Sealed this
First Day of September, 2020

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 34
<212> TYPE: PRT
<213> ORGANISM: Artificial Sequence
<220> FEATURE:
<223> OTHER INFORMATION: Synthetic

<400> SEQUENCE: 1

Asn Met Ser Val Leu Val Tyr Ser Phe Ala Ser Phe Val Leu Gly Trp
1               5                   10                  15

Cys Leu Arg Ser Gly Ile Thr Tyr Phe Thr Arg Leu Met Glu Thr Ser
            20                  25                  30

Ser Cys

<210> SEQ ID NO 2
<211> LENGTH: 99
<212> TYPE: DNA
<213> ORGANISM: Artificial Sequence
<220> FEATURE:
<223> OTHER INFORMATION: Synthetic

<400> SEQUENCE: 2
atgagtgttt tagtgtattc tttcgcctct ttcgttttag gttggtgcct tcgtagtggc      60
```

```
attacgtatt ttacccgttt aatggaaact tcctcatga                            99

<210> SEQ ID NO 3
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Asn Met Ser Gln Xaa Gln Val Leu Val Tyr Ser Phe Ala Ser Phe Val
1               5                   10                  15

Leu Gly Trp Cys Leu Arg Ser Gly Ile Thr Tyr Phe Thr Arg Leu Met
            20                  25                  30

Glu Thr Ser Ser Cys
        35

<210> SEQ ID NO 4
<211> LENGTH: 106
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t

<400> SEQUENCE: 4
atgagttagn taggttttag tgtattcttt cgcctctttc gttttaggtt ggtgccttcg    60
tagtggcatt acgtatttta cccgtttaat ggaaacttcc tcatga                 106

<210> SEQ ID NO 5
<211> LENGTH: 49
<212> TYPE: DNA
<213> ORGANISM: Artificial Sequence
<220> FEATURE:
<223> OTHER INFORMATION: Synthetic

<400> SEQUENCE: 5
gctgggggtc aaagatgagt tagagctagg ttttagtgta ttctttcgc               49

<210> SEQ ID NO 6
<211> LENGTH: 49
<212> TYPE: DNA
<213> ORGANISM: Artificial Sequence
<220> FEATURE:
<223> OTHER INFORMATION: Synthetic

<400> SEQUENCE: 6
gcgaaagaat acactaaaac ctagctctaa ctcatctttg accccagc                49

<210> SEQ ID NO 7
<211> LENGTH: 8669
<212> TYPE: DNA
<213> ORGANISM: Artificial Sequence
<220> FEATURE:
<223> OTHER INFORMATION: Synthetic

<400> SEQUENCE: 7
tgcctgactc cccgtcgtgt agataactac gatacgggag ggcttaccat ctggccccag    60
```

```
tgctgcaatg ataccgcgag acccacgctc accggctcca gatttatcag caataaacca      120
gccagccgat tcgagctcgc ccggggatcg accagttggt gattttgaac ttttgctttg      180
ccacggaacg gtctgcgttg tcgggaagat gcgtgatctg atccttcaac tcagcaaaag      240
ttcgatttat tcaacaaagc cgccgtcccg tcaagtcagc gtaatgctct gccagtgtta      300
caaccaatta accaattctg attagaaaaa ctcatcgagc atcaaatgaa actgcaattt      360
attcatatca ggattatcaa taccatattt ttgaaaaagc cgtttctgta atgaaggaga      420
aaactcaccg aggcagttcc ataggatggc aagatcctgg tatcggtctg cgattccgac      480
tcgtccaaca tcaatacaac ctattaattt cccctcgtca aaataaggt tatcaagtga       540 gaaatcacca tgagtgacga ctgaatccgg tgagaatggc aaaagcttat gcatttcttt      600
ccagacttgt tcaacaggcc agccattacg ctcgtcatca aaatcactcg catcaaccaa      660
accgttattc attcgtgatt gcgcctgagc gagacgaaat acgcgatcgc tgttaaaagg      720
acaattacaa acaggaatcg aatgcaaccg gcgcaggaac actgccagcg catcaacaat      780
attttcacct gaatcaggat attcttctaa tacctggaat gctgttttcc cggggatcgc      840
agtggtgagt aaccatgcat catcaggagt acggataaaa tgcttgatgg tcggaagagg      900
cataaattcc gtcagccagt ttagtctgac catctcatct gtaacatcat ggcaacgct       960 acctttgcca tgtttcagaa acaactctgg cgcatcgggc ttcccataca atcgatagat     1020
tgtcgcacct gattgcccga cattatcgcg agcccattta tacccatata aatcagcatc     1080
catgttggaa tttaatcgcg gcctcgagca agacgtttcc cgttgaatat ggctcataac     1140 ccccttgta ttactgttta tgtaagcaga cagttttatt gttcatgatg atatatttt      1200 atcttgtgca atgtaacatc agagattttg aaacacaacg tggctttccc cccccccc       1260 ctgcaggtct cgggctattc ttttgattta aagggattt tgccgatttc ggctattgg      1320 ttaaaaatg agctgattta acaaaaattt aacgcgaatt ttaacaaaat attaacgttt      1380
acaatttaaa tatttgctta tacaatcttc ctgttttttgg ggcttttctt attatcaacc     1440
ggggtacata tgattgacat gctagtttta cgattaccgt tcatcgattc tcttgtttgc     1500
tccagactct caggcaatga cctgatagcc tttgtagacc tctcaaaaat agctaccctc     1560
tccggcatga atttatcagc tagaacggtt gaatatcatg ttgatggtga tttgactgtc     1620
tccgcctttt ctcacccttt tgaatcttta cctacacatt actcaggcat tgcatttaaa     1680
atatatgagg gttctaaaaa ttttatcct tgcgttgaaa taaaggcttc tcccgcaaaa     1740
gtattacagg gtcataatgt ttttggtaca accgatttag ctttatgctc tgaggcttta     1800
ttgcttaatt ttgctaattc tttgccttgc ctgtatgatt tattggatgt taacgctact     1860
actattagta gaattgatgc cacctttca gctcgcgccc caaatgaaaa tatagctaaa     1920
caggttattg accatttgcg aaatgtatct aatggtcaaa ctaaatctac tcgttcgcag     1980
aattgggaat caactgttac atggaatgaa acttccagac accgtacttt agttgcatat     2040
ttaaaacatg ttgagctaca gcaccagatt cagcaattaa gctctaagcc atccgcaaaa     2100
atgacctctt atcaaaagga gcaattaaag gtactctcta atcctgacct gttggagttt     2160
gcttccggtc tggttcgctt tgaagctcga attaaaacgc gatatttgaa gtctttcggg     2220
cttcctctta atctttttga tgcaatccgc tttgcttctg actataatag tcagggtaaa     2280
gacctgattt ttgatttatg gtcattctcg ttttctgaac tgtttaaagc atttgagggg     2340
gattcaatga atatttatga cgattccgca gtattggacg ctatccagtc taaacatttt     2400
actattaccc cctctggcaa aacttctttt gcaaaagcct ctcgctattt tggttttat     2460
```

```
cgtcgtctgg taaacgaggg ttatgatagt gttgctctta ctatgcctcg taattccttt    2520
tggcgttatg tatctgcatt agttgaatgt ggtattccta aatctcaact gatgaatctt    2580
tctacctgta ataatgttgt tccgttagtt cgttttatta acgtagattt ttcttcccaa    2640
cgtcctgact ggtataatga gccagttctt aaaatcgcat aaggtaattc acaatgatta    2700
aagttgaaat taaaccatct caagcccaat ttactactcg ttctggtgtt tctcgtcagg    2760
gcaagcctta ttcactgaat gagcagcttt gttacgttga tttgggtaat gaatatccgg    2820
ttcttgtcaa gattactctt gatgaaggtc agccagccta tgcgcctggt ctgtacaccg    2880
ttcatctgtc ctcttccaaa gttggtcagt tcggttccct tatgattgac cgtctgcgcc    2940
tcgttccggc taagtaacat ggagcaggtc gcggatttcg acacaattta tcaggcgatg    3000
atacaaatct ccgttgtact ttgtttcgcg cttggtataa tcgctggggg tcaaagatga    3060
gtgttttagt gtattctttc gcctctttcg ttttaggttg gtgccttcgt agtggcatta    3120
cgtattttac ccgtttaatg gaaacttcct catgaaaaag tctttagtcc tcaaagcctc    3180
tgtagccgtt gctaccctcg ttccgatgct gtctttcgct gctgagggtg acgatcccgc    3240
aaaagcggcc tttaactccc tgcaagcctc agcgaccgaa tatatcggtt atgcgtgggc    3300
gatggttgtt gtcattgtcg gcgcaactat cggtatcaag ctgtttaaga aattcacctc    3360
gaaagcaagc tgataaaccg atacaattaa aggctccttt tggagccttt ttttttggag    3420
attttcaacg tgaaaaaatt attattcgca attcctttag ttgttccttt ctattctcac    3480
tccgctgaaa ctgttgaaag ttgtttagca aaaccccata cagaaaattc atttactaac    3540
gtctggaaag acgacaaaac tttagatcgt tacgctaact atgagggctg tctgtggaat    3600
gctacaggcg ttgtagtttg tactggtgac gaaactcagt gttacggtac atgggttcct    3660
attgggcttg ctatccctga aaatgagggt ggtggctctg agggtggcgg ttctgagggt    3720
ggcggttctg agggtggcgg tactaaacct cctgagtacg tgatacacc tattccgggc    3780 tatacttata tcaaccctct cgacggcact tatccgcctg gtactgagca aaaccccgct    3840
aatcctaatc cttctcttga ggagtctcag cctcttaata ctttcatgtt tcagaataat    3900
aggttccgaa ataggcaggg ggcattaact gtttatacgg gcactgttac tcaaggcact    3960
gaccccgtta aaacttatta ccagtacact cctgtatcat caaaagccat gtatgacgct    4020
tactggaacg gtaaattcag agactgcgct ttccattctg gctttaatga ggatccattc    4080
gtttgtgaat atcaaggcca atcgtctgac ctgcctcaac ctcctgtcaa tgctggcggc    4140
ggctctggtg gtggttctgg tggcggctct gagggtggtg gctctgaggg tggcggttct    4200
gagggtggcg gctctgaggg aggcggttcc ggtggtggct ctggttccgg tgattttgat    4260
tatgaaaaga tggcaaacgc taataagggg gctatgaccg aaaatgccga tgaaaacgcg    4320
ctacagtctg acgctaaagg caaacttgat tctgtcgcta ctgattacgg tgctgctatc    4380
gatggtttca ttggtgacgt ttccggcctt gctaatggta atggtgctac tggtgatttt    4440
gctggctcta attcccaaat ggctcaagtc ggtgacggtg ataattcacc tttaatgaat    4500
aatttccgtc aatatttacc ttccctccct caatcggttg aatgtcgccc ttttgtcttt    4560
ggcgctggta accatatga attttctatt gattgtgaca aaataaactt attccgtggt    4620
gtctttgcgt ttcttttata tgttgccacc tttatgtatg tattttctac gtttgctaac    4680
atactgcgta ataaggagtc ttaatcatgc cagttctttt gggtattccg ttattattgc    4740
gtttcctcgg tttccttctg gtaactttgt tcggctatct gcttactttt cttaaaaagg    4800
```

```
gcttcggtaa gatagctatt gctatttcat tgtttcttgc tcttattatt gggcttaact    4860
caattcttgt gggttatctc tctgatatta gcgctcaatt accctctgac tttgttcagg    4920
gtgttcagtt aattctcccg tctaatgcgc ttccctgttt ttatgttatt ctctctgtaa    4980
aggctgctat tttcattttt gacgttaaac aaaaaatcgt ttcttatttg gattgggata    5040
aataatatgg ctgtttattt tgtaactggc aaattaggct ctggaaagac gctcgttagc    5100
gttggtaaga ttcaggataa aattgtagct gggtgcaaaa tagcaactaa tcttgattta    5160
aggcttcaaa acctcccgca agtcgggagg ttcgctaaaa cgcctcgcgt tcttagaata    5220
ccggataagc cttctatatc tgatttgctt gctattgggc gcggtaatga ttcctacgat    5280
gaaaataaaa acggcttgct tgttctcgat gagtgcggta cttggtttaa tacccgttct    5340
tggaatgata aggaaagaca gccgattatt gattggtttc tacatgctcg taaattagga    5400
tgggatatta ttttcttgt tcaggactta tctattgttg ataaacaggc gcgttctgca    5460
ttagctgaac atgttgttta ttgtcgtcgt ctggacagaa ttactttacc ttttgtcggt    5520
actttatatt ctcttattac tggctcgaaa atgcctctgc ctaaattaca tgttggcgtt    5580
gttaaatatg gcgattctca attaagcccT actgttgagc gttggcttta tactggtaag    5640
aatttgtata acgcatatga tactaaacag cttttttcta gtaattatga ttccggtgtt    5700
tattcttatt taacgcctta tttatcacac ggtcggtatt tcaaaccatt aaatttaggt    5760
cagaagatga aattaactaa aatatatttg aaaaagtttt ctcgcgttct ttgtcttgcg    5820
attggatttg catcagcatt tacatatagt tatataaccc aacctaagcc ggaggttaaa    5880
aaggtagtct ctcagaccta tgattttgat aaattcacta ttgactcttc tcagcgtctt    5940
aatctaagct atcgctatgt tttcaaggat tctaagggaa aattaattaa tagcgacgat    6000
ttacagaagc aaggttattc actcacatat attgatttat gtactgtttc cattaaaaaa    6060
ggtaattcaa atgaaattgt taaatgtaat taattttgtt ttcttgatgt ttgtttcatc    6120
atcttctttt gctcaggtaa ttgaaatgaa taattcgcct ctgcgcgatt ttgtaacttg    6180
gtattcaaag caatcaggcg aatccgttat tgtttctccc gatgtaaaag gtactgttac    6240
tgtatattca tctgacgtta aacctgaaaa tctacgcaat ttctttatt ctgttttacg    6300 tgcaaataat tttgatatgg taggttctaa cccttccatt attcagaagt ataatccaaa    6360
caatcaggat tatattgatg aattgccatc atctgataat caggaatatg atgataattc    6420
cgctccttct ggtggtttct ttgttccgca aaatgataat gttactcaaa cttttaaaat    6480
taataacgtt cgggcaaagg atttaatacg agttgtcgaa ttgtttgtaa agtctaatac    6540
ttctaaatcc tcaaatgtat tatctattga cggctctaat ctattagttg ttagtgctcc    6600
taaagatatt ttagataacc ttcctcaatt cctttcaact gttgatttgc caactgacca    6660
gatattgatt gagggtttga tatttgaggt tcagcaaggt gatgctttag attttcatt    6720 tgctgctggc tctcagcgtg gcactgttgc aggcggtgtt aatactgacc gcctcacctc    6780
tgttttatct tctgctggtg gttcgttcgg tattttaat ggcgatgttt tagggctatc    6840
agttcgcgca ttaaagacta atagccattc aaaaatattg tctgtgccac gtattcttac    6900
gctttcaggt cagaagggtt ctatctctgt tggccagaat gtcccttta ttactggtcg    6960 tgtgactggt gaatctgcca atgtaaataa tccatttcag acgattgagc gtcaaaatgt    7020
aggtatttcc atgagcgttt ttcctgttgc aatggctggc ggtaatattg ttctggatat    7080
taccagcaag gccgatagtt tgagttcttc tactcaggca agtgatgtta ttactaatca    7140
aagaagtatt gctacaacgg ttaatttgcg tgatggacag actcttttac tcggtggcct    7200
```

```
cactgattat aaaaacactt ctcaggattc tggcgtaccg ttcctgtcta aatcccttt    7260 aatcggcctc ctgtttagct cccgctctga ttctaacgag gaaagcacgt tatacgtgct   7320
cgtcaaagca accatagtac gcgccctgta gcggcgcatt aagcgcggcg ggtgtggtgg   7380
ttacgcgcag cgtgaccgct acacttgcca gcgccctagc gcccgctcct ttcgctttct   7440
tcccttcctt tctcgccacg ttcgccggct ttccccgtca gctctaaat cggggggctcc   7500 ctttagggtt ccgatttagt gctttacggc acctcgaccc caaaaaactt gatttgggtg   7560
atggttcacg tagtgggcca tcgccctgat agacggtttt cgccctttg acgttggagt    7620 ccacgttctt taatagtgga ctcttgttcc aaactgaac aacactcaac cctatctcgg     7680
gacggatcgc ttcatgtggc aggagaaaaa aggctgcacc ggtgcgtcag cagaatatgt    7740
gatacaggat atattccgct tcctcgctca ctgactcgct acgctcggtc gttcgactgc    7800
ggcgagcgga aatggcttac gaacggggcg gagatttcct ggaagatgcc aggaagatac    7860
ttaacaggga agtgagaggg ccgcggcaaa gccgttttc cataggctcc gcccccctga     7920
caagcatcac gaaatctgac gctcaaatca gtggtggcga acccgacag gactataaag     7980 ataccaggcg tttccccctg gcggctccct cgtgcgctct cctgttcctg cctttcggtt    8040
taccggtgtc attccgctgt tatggccgcg tttgtctcat tccacgcctg acactcagtt    8100
ccgggtaggc agttcgctcc aagctggact gtatgcacga accccccgtt cagtccgacc    8160
gctgcgcctt atccggtaac tatcgtcttg agtccaaccc ggaaagacat gcaaaagcac    8220
cactggcagc agccactggt aattgattta gaggagttag tcttgaagtc atgcgccggt    8280
taaggctaaa ctgaaaggac aagttttggt gactgcgctc ctccaagcca gttacctcgg    8340
ttcaaagagt tggtagctca gagaaccttc gaaaaccgc cctgcaaggc ggttttttcg     8400
ttttcagagc aagagattac gcgcagacca aaacgatctc aagaagatca tcttattaag    8460
gggtctgacg ctcagtggaa cgaaaactca cgttaaggga ttttggtcat gagattatca    8520
aaaaggatct tcacctagat ccttttaaat taaaaatgaa gttttaaatc aatctaaagt    8580
atatatgagt aaacttggtc tgacagttac caatgcttaa tcagtgaggc acctatctca    8640
gcgatctgtc tatttcgttc atccatagt                                      8669

<210> SEQ ID NO 8
<211> LENGTH: 68
<212> TYPE: DNA
<213> ORGANISM: Artificial Sequence
<220> FEATURE:
<223> OTHER INFORMATION: Synthetic

<400> SEQUENCE: 8
ccggctaagt aacatggagc agcaaagatg agtgttttag tgttaatgga aacttcctca    60
tgaaaaag                                                              68

<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Pro Ala Lys Met Glu Gln Gln Arg Met Ser Val Leu Val Leu Met Glu
1               5                   10                  15

Thr Ser Ser Met Lys Lys
```

```
                        20

<210> SEQ ID NO 10
<211> LENGTH: 77
<212> TYPE: DNA
<213> ORGANISM: Artificial Sequence
<220> FEATURE:
<223> OTHER INFORMATION: Synthetic

<400> SEQUENCE: 10
ccggctaagt aacatggagc agcaaagatg agttagagct aggttttagt gttaatggaa      60
acttcctcat gaaaaag                                                    77

<210> SEQ ID NO 11
<211> LENGTH: 25
<212> TYPE: PRT
<213> ORGANISM: Artificial Sequence
<220> FEATURE:
<223> OTHER INFORMATION: Synthetic

<400> SEQUENCE: 11

Pro Ala Lys Met Glu Gln Gln Arg Met Ser Gln Ser Gln Val Leu Val
1               5                   10                  15

Leu Met Glu Thr Ser Ser Met Lys Lys
            20                  25
```